(12) United States Patent
Zeiner et al.

(10) Patent No.: US 9,084,599 B2
(45) Date of Patent: Jul. 21, 2015

(54) SURGICAL STAPLING INSTRUMENT FOR APPLYING A LARGE STAPLE THROUGH A SMALL DELIVERY PORT AND A METHOD OF USING THE SURGICAL STAPLER TO SECURE A TISSUE FOLD

(75) Inventors: Mark S. Zeiner, Mason, OH (US);
Michael J. Stokes, Cincinnati, OH (US);
Jason L. Harris, Mason, OH (US);
Daniel E. Alesi, Lebanon, OH (US);
Lawrence Crainich, Charlestown, NH (US)

(73) Assignee: ETHICON ENDO-SURGERY, INC., Cincinnati, OH (US)

( * ) Notice: Subject to any disclaimer, the term of this patent is extended or adjusted under 35 U.S.C. 154(b) by 1699 days.

(21) Appl. No.: 12/113,829

(22) Filed: May 1, 2008

(65) Prior Publication Data
US 2009/0272786 A1    Nov. 5, 2009

(51) Int. Cl.
| | |
|---|---|
| *A61B 17/068* | (2006.01) |
| *A61B 17/00* | (2006.01) |
| *A61B 17/64* | (2006.01) |
| *A61B 17/29* | (2006.01) |

(52) U.S. Cl.
CPC ......... *A61B 17/068* (2013.01); *A61B 17/00234* (2013.01); *A61B 17/0684* (2013.01); *A61B 17/6425* (2013.01); *A61B 2017/0034* (2013.01); *A61B 2017/00818* (2013.01); *A61B 2017/2929* (2013.01)

(58) Field of Classification Search
USPC ................................ 227/175.1, 175.3, 181.1
See application file for complete search history.

(56) References Cited

U.S. PATENT DOCUMENTS

| | | | | |
|---|---|---|---|---|
| 4,261,244 A | * | 4/1981 | Becht et al. | 411/472 |
| 4,821,721 A | * | 4/1989 | Chin et al. | 606/143 |
| 5,192,288 A | * | 3/1993 | Thompson et al. | 606/143 |
| 5,203,785 A | * | 4/1993 | Slater | 606/205 |
| 5,282,808 A | * | 2/1994 | Kovac et al. | 606/143 |
| 5,308,576 A | * | 5/1994 | Green et al. | 419/38 |
| 5,340,360 A | * | 8/1994 | Stefanchik | 606/142 |
| 5,342,396 A | * | 8/1994 | Cook | 606/219 |
| 5,392,978 A | | 2/1995 | Velez et al. | |
| 5,478,003 A | * | 12/1995 | Green et al. | 227/176.1 |
| 5,484,095 A | * | 1/1996 | Green et al. | 227/181.1 |
| 5,582,611 A | | 12/1996 | Tsuruta et al. | |

(Continued)

FOREIGN PATENT DOCUMENTS

| | | |
|---|---|---|
| WO | 2005/115251 | 12/2005 |
| WO | WO2005115251 | 12/2005 |

*Primary Examiner* — Gloria R Weeks
(74) *Attorney, Agent, or Firm* — Welsh Flaxman & Gitler LLC

(57) ABSTRACT

A low-profile surgical stapler enables a large-sized staple to be delivered into a body cavity through a small opening or port. The surgical stapler includes a handle having a trigger movably coupled to the handle. The surgical stapler also includes an elongated, tubular shaft extends distally from the handle. The tubular shaft includes a proximal end secured to the handle and a distal end in which a deployment opening is formed. A staple deploying assembly is disposed within an interior of the shaft for discharging staples from the deployment opening at the distal end of the shaft, the staple deploying assembly supporting a staple such that a longitudinal axis of the staple is aligned with a longitudinal axis of the shaft. The deployment opening is shaped and dimensioned to permit the deployment of the staples from within the shaft, out of the deployment opening and into adjacent tissue.

14 Claims, 31 Drawing Sheets

(56) References Cited

U.S. PATENT DOCUMENTS

| | | | |
|---|---|---|---|
| 5,601,573 A * | 2/1997 | Fogelberg et al. | 606/143 |
| 5,681,330 A * | 10/1997 | Hughett et al. | 606/143 |
| 5,738,474 A * | 4/1998 | Blewett | 411/473 |
| 5,782,396 A * | 7/1998 | Mastri et al. | 227/175.3 |
| 5,782,397 A * | 7/1998 | Koukline | 227/176.1 |
| 5,797,538 A * | 8/1998 | Heaton et al. | 227/176.1 |
| 5,797,838 A * | 8/1998 | Oka | 600/300 |
| 5,820,009 A * | 10/1998 | Melling et al. | 227/176.1 |
| 5,829,662 A | 11/1998 | Allen et al. | |
| 5,833,700 A * | 11/1998 | Fogelberg et al. | 606/158 |
| 6,494,886 B1 * | 12/2002 | Wilk et al. | 606/142 |
| 6,652,539 B2 * | 11/2003 | Shipp et al. | 606/143 |
| 6,877,647 B2 * | 4/2005 | Green et al. | 227/176.1 |
| 7,401,720 B1 * | 7/2008 | Durrani | 227/176.1 |
| 7,530,484 B1 * | 5/2009 | Durrani | 227/176.1 |
| 7,641,091 B2 * | 1/2010 | Olson et al. | 227/175.1 |
| 7,669,746 B2 * | 3/2010 | Shelton, IV | 227/175.1 |
| 2004/0167573 A1 | 8/2004 | Williamson et al. | |
| 2006/0253143 A1 | 11/2006 | Edoga et al. | |
| 2006/0291981 A1 * | 12/2006 | Viola et al. | 411/457 |
| 2007/0083234 A1 * | 4/2007 | Shelton et al. | 606/219 |
| 2007/0131732 A1 * | 6/2007 | Holsten et al. | 227/179.1 |
| 2009/0321496 A1 * | 12/2009 | Holsten et al. | 227/180.1 |
| 2011/0042440 A1 * | 2/2011 | Holsten et al. | 227/176.1 |

* cited by examiner

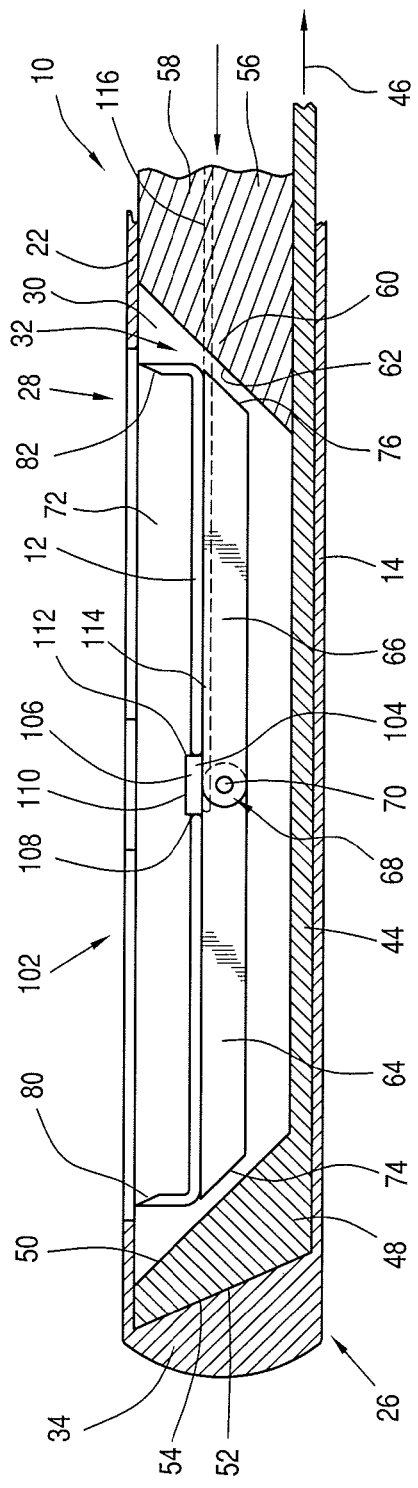
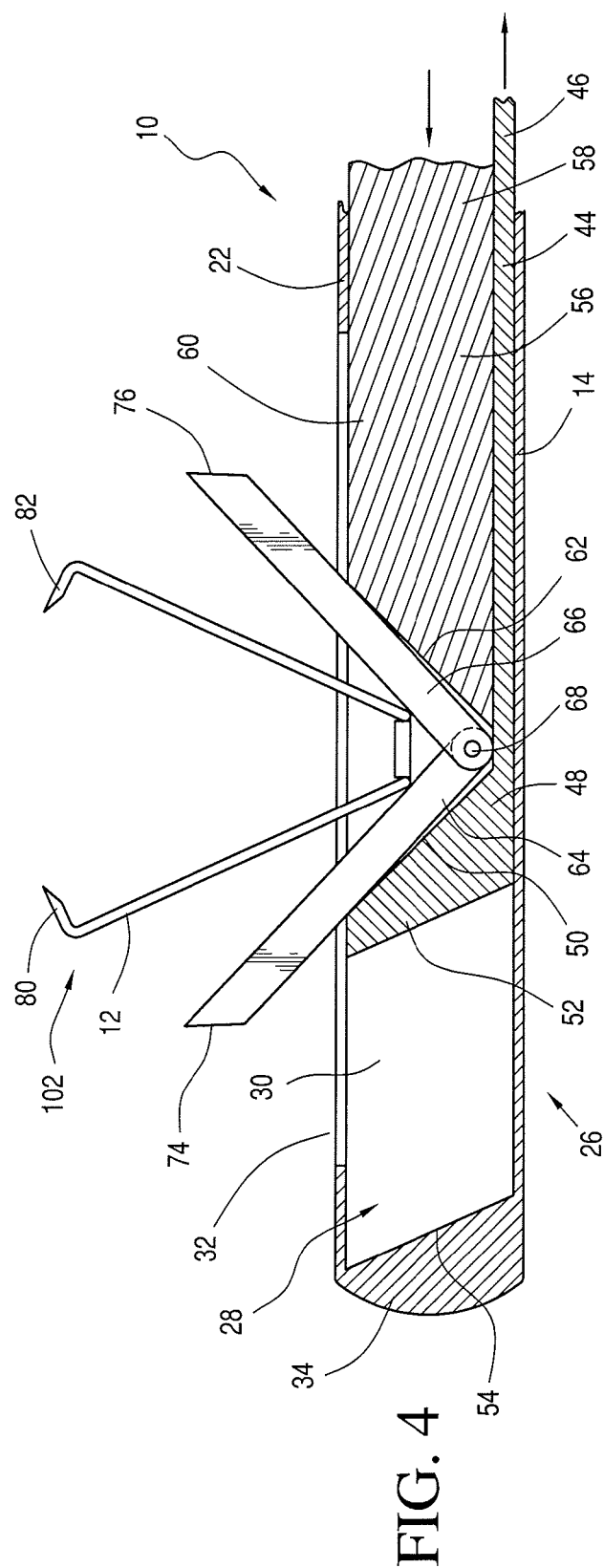
FIG. 2
FIG. 4

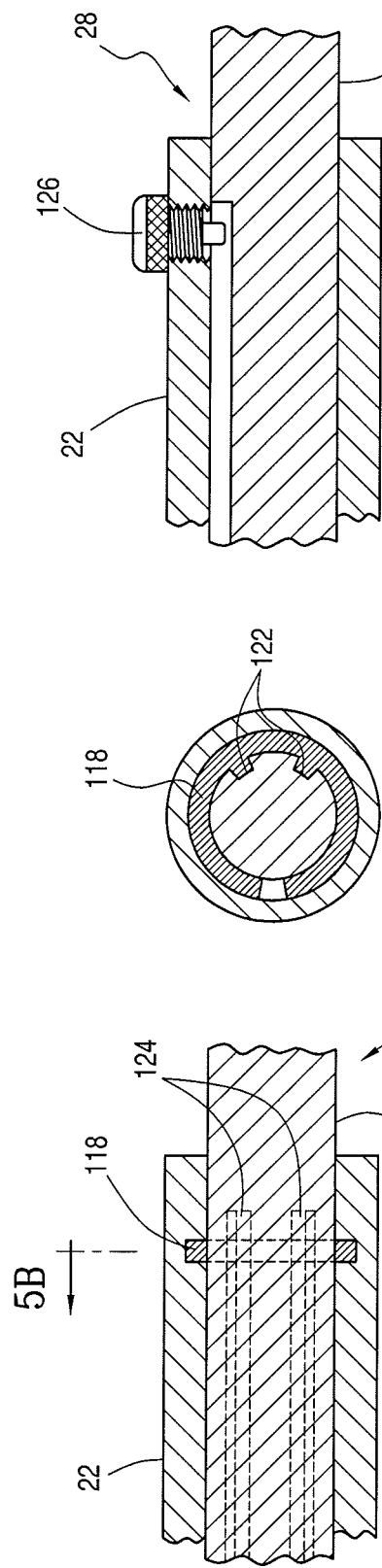
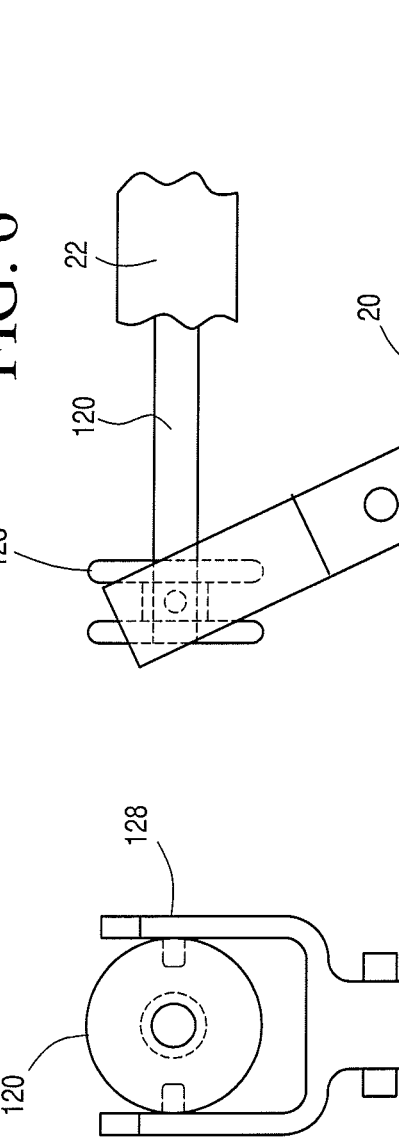
FIG. 5A
FIG. 5B
FIG. 6
FIG. 7A
FIG. 7B

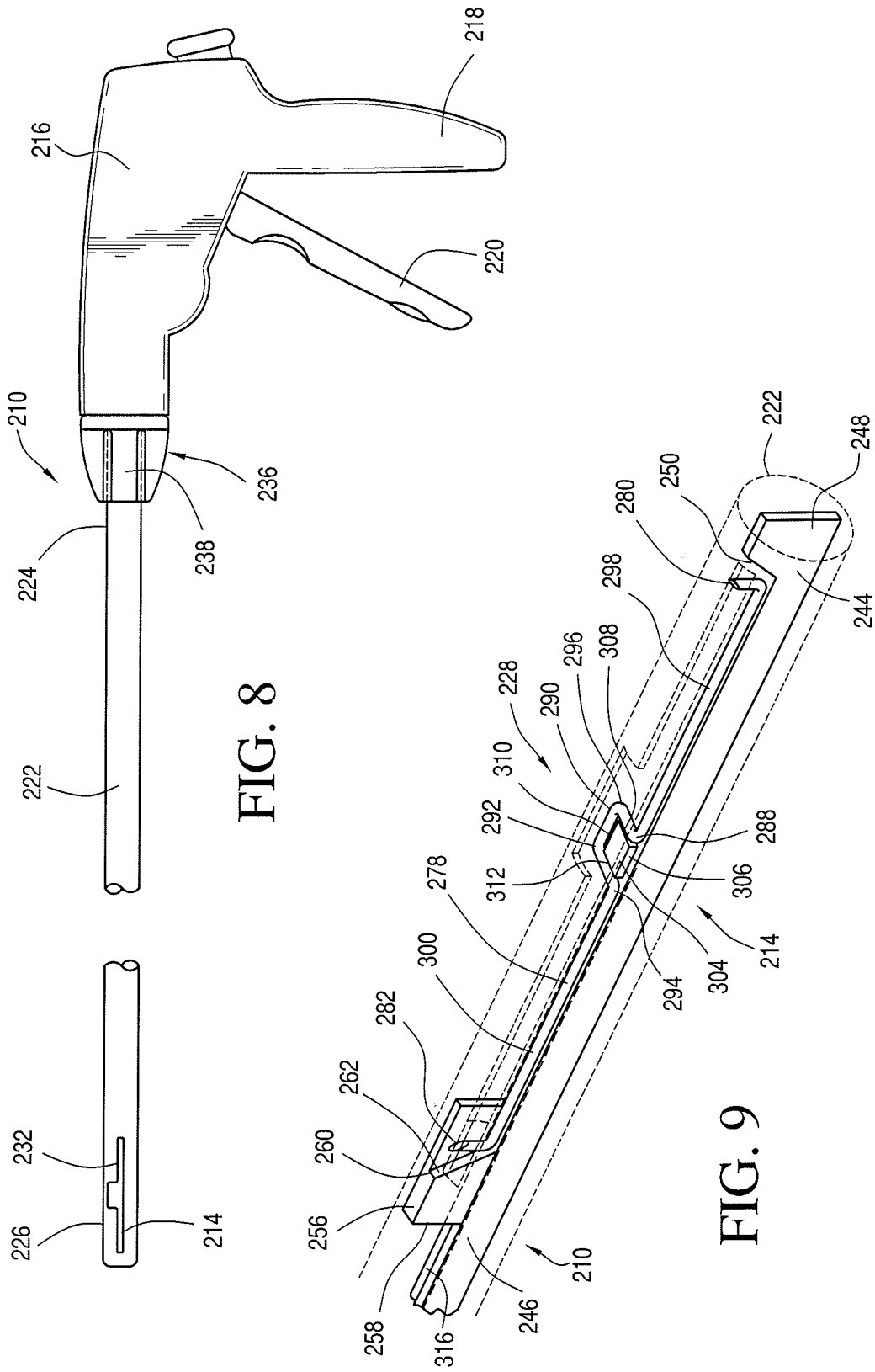

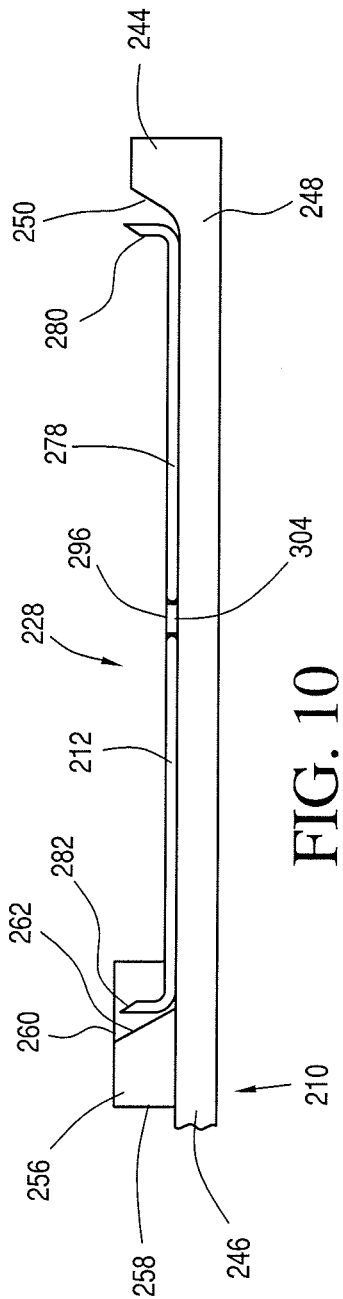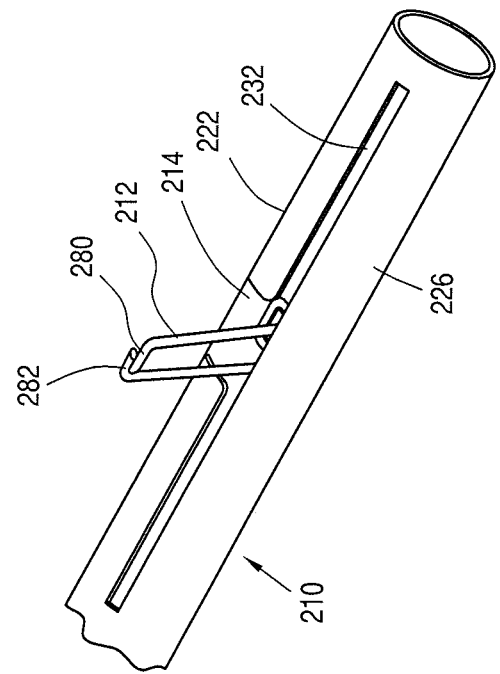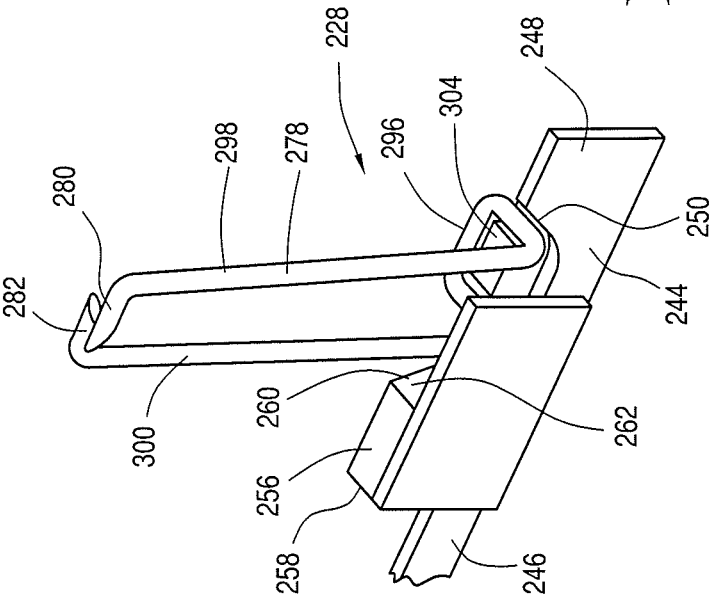
FIG. 10
FIG. 11
FIG. 12

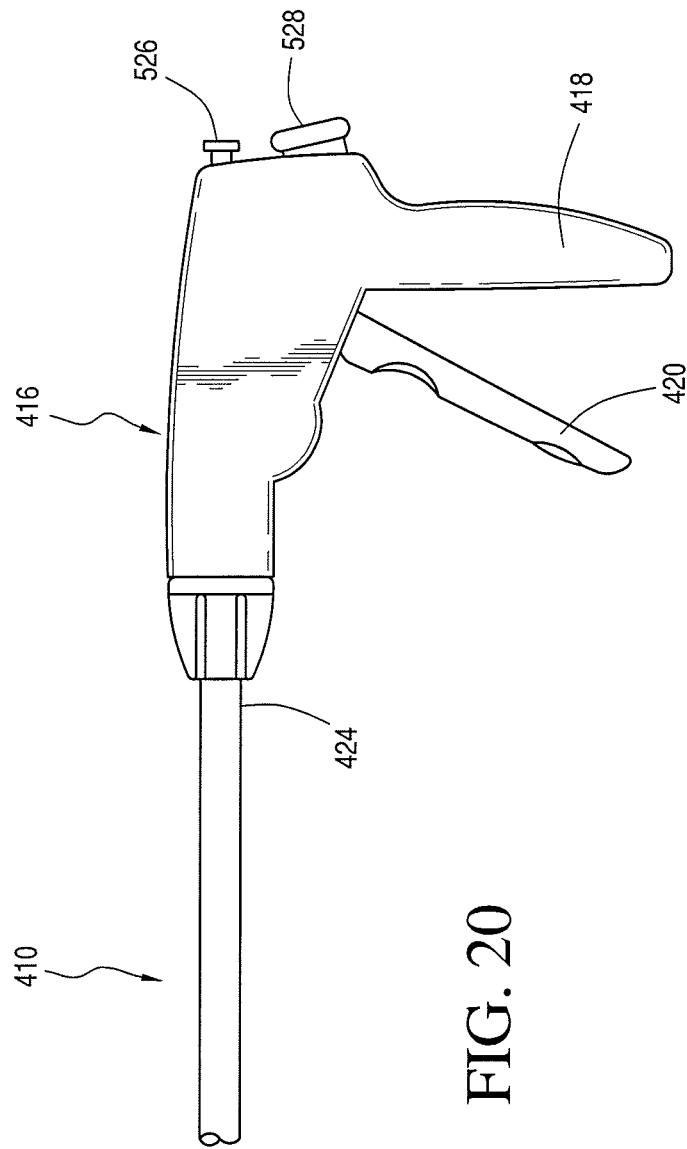
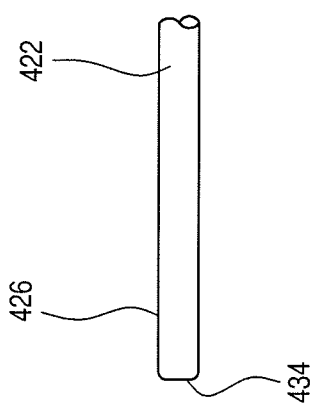
FIG. 20

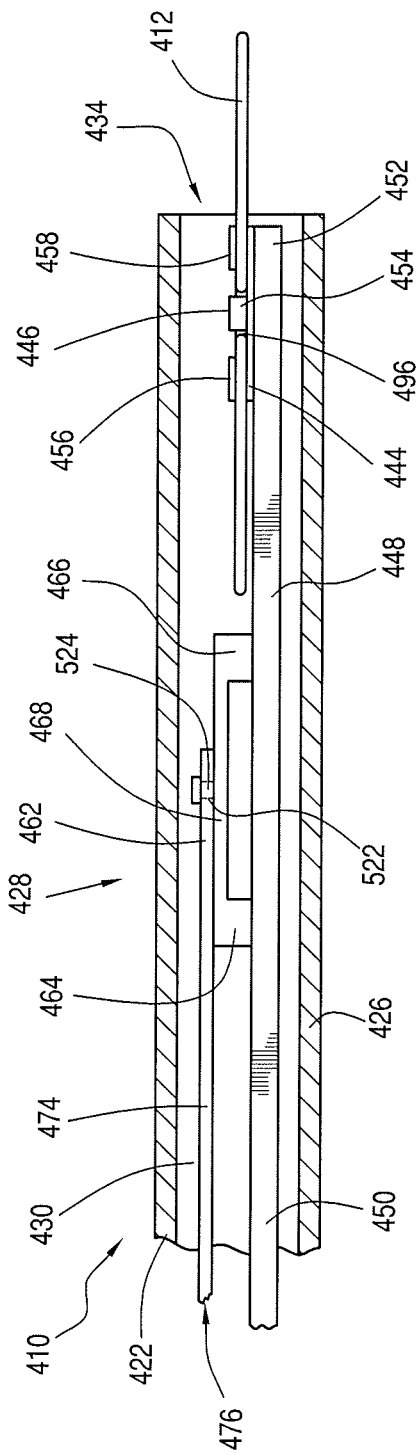
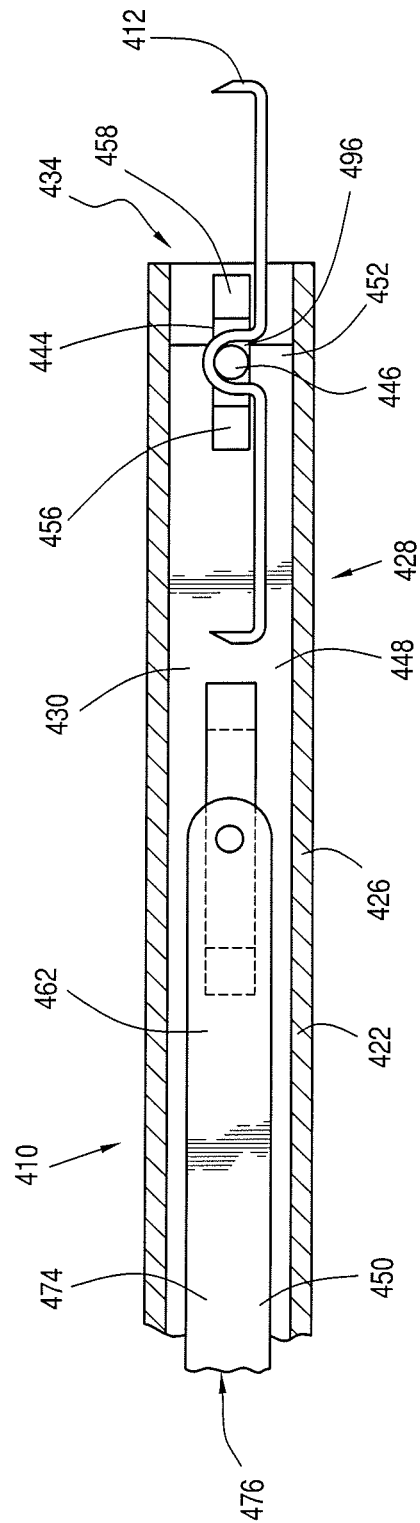
FIG. 21a
FIG. 21b

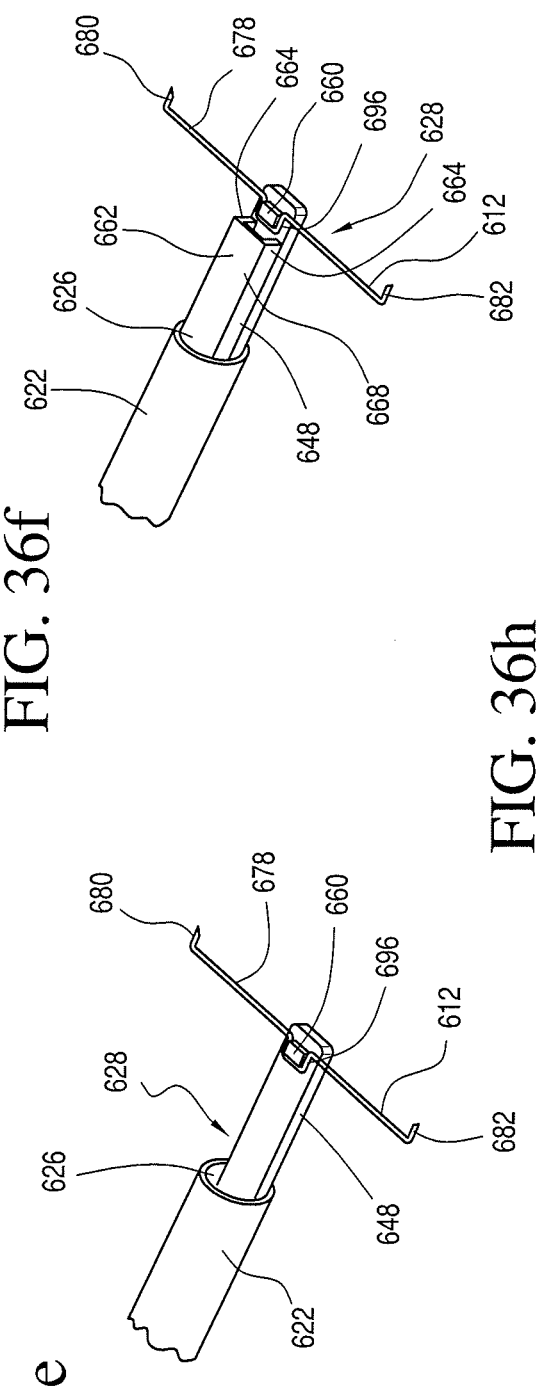
FIG. 36e
FIG. 36f
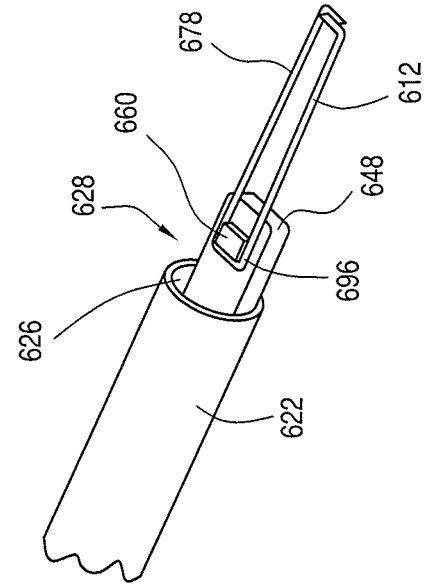
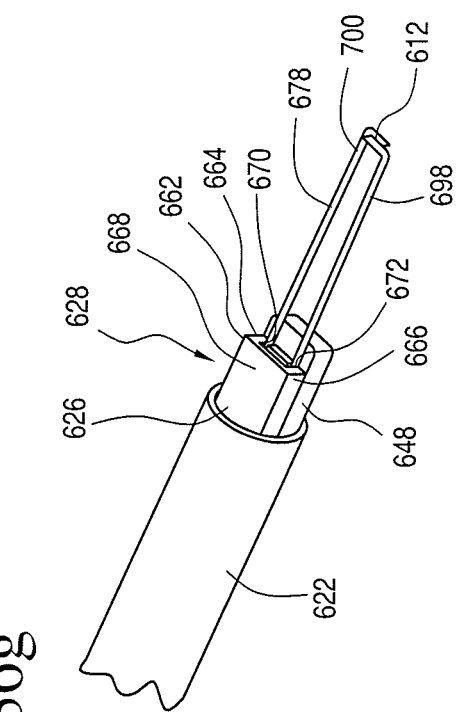
FIG. 36g
FIG. 36h

SURGICAL STAPLING INSTRUMENT FOR APPLYING A LARGE STAPLE THROUGH A SMALL DELIVERY PORT AND A METHOD OF USING THE SURGICAL STAPLER TO SECURE A TISSUE FOLD

BACKGROUND OF THE INVENTION

1. Field of the Invention

The present invention generally relates to the apposition of tissue within a body cavity. More particularly, the present invention relates to a low profile surgical stapler for delivering a large staple to a body cavity through either a small trocar port or a flexible endoscope. The present invention also relates to methods of using the low profile surgical stapler to secure tissues together within a body cavity during bariatric surgery.

2. Description of the Related Art

Obesity is a medical condition affecting more than 30% of the population in the United States. Obesity affects an individual's personal quality of life and contributes significantly to morbidity and mortality. Obese patients, i.e. individuals having a body mass index ("BMI") greater than 30, often have a high risk of associated health problems (e.g., diabetes, hypertension, and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients. Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, RYGB, gastric banding or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

With the foregoing in mind, it is desirable to provide surgical weight loss procedures (and related medical instruments) that are inexpensive, with few potential complications, and that provide patients with a weight loss benefit while buying time for the lifestyle changes necessary to maintain the weight loss. Further, it is desirable that the procedures be minimally invasive to the patient, allowing for a quick recovery and less scarring. The present invention provides a medical instrument allowing for the performance of surgical weight loss procedures in an efficient and effective manner.

SUMMARY OF THE INVENTION

It is, therefore, an object of the present invention to provide a low-profile surgical stapler that enables a large-sized staple to be delivered into a body cavity through a small opening or port. The surgical stapler includes a handle having a trigger movably coupled to the handle. The surgical stapler also includes an elongated, tubular shaft extends distally from the handle. The tubular shaft includes a proximal end secured to the handle and a distal end in which a deployment opening is formed. A staple deploying assembly is disposed within an interior of the shaft for discharging staples from the deployment opening at the distal end of the shaft, the staple deploying assembly supporting a staple such that a longitudinal axis of the staple is aligned with a longitudinal axis of the shaft. The deployment opening is shaped and dimensioned to permit the deployment of the staples from within the shaft, out of the deployment opening and into adjacent tissue.

It is also an object of the present invention to provide a surgical stapler wherein the shaft has a diameter that is less than approximately 5 mm.

It is another object of the present invention to provide a surgical stapler wherein the shaft is rotatably secured to the handle.

It is a further object of the present invention to provide a surgical stapler wherein rotation of the shaft is coordinated with rotation of the staple deploying assembly.

It is also an object of the present invention to provide a surgical stapler wherein the staple deploying assembly includes a first staple driver and a second staple driver extending longitudinally through the shaft.

It is another object of the present invention to provide a surgical stapler wherein the first staple driver includes a camming surface that is shaped to act upon a staple and the second staple driver includes a camming surface shaped to act upon a staple.

It is a further object of the present invention to provide a surgical stapler wherein first and second bending arms are longitudinally disposed in the shaft and oriented in a manner facing the deployment opening such that a staple may be supported thereon during folding and subsequent ejection from the deployment opening.

It is also an object of the present invention to provide a surgical stapler wherein the first staple driver includes a camming surface that is shaped to act upon the first bending arm and the second staple driver includes a camming surface shaped to act upon the second bending arm.

It is another object of the present invention to provide a surgical stapler wherein a staple includes a long body segment having a longitudinal axis, first and second prongs are found at opposite ends of the body segment and extend in a direction that is substantially transverse to the longitudinal axis of the body segment.

It is a further object of the present invention to provide a surgical stapler wherein the body segment includes a box at a center of the staple.

It is also an object of the present invention to provide a surgical stapler wherein the staple deploying assembly includes a post shaped and dimensioned to support the staple at the box.

It is another object of the present invention to provide a surgical stapler including a locking bar which selectively slides over the support post and staple to lock the staple in place prior to firing.

It is a further object of the present invention to provide a surgical stapler wherein the deployment opening is at a distal tip of the shaft.

It is also an object of the present invention to provide a surgical stapler wherein the staple deploying assembly includes an anvil including a center support that engages the staple to hold the staple during transport through the shaft.

It is another object of the present invention to provide a surgical stapler wherein the anvil includes first and second bending guides providing a structure around which the staple is formed during deployment.

It is a further object of the present invention to provide a surgical stapler wherein the staple deploying assembly includes a staple former includes first and second forming blocks attached on opposite sides of a connecting member.

It is also an object of the present invention to provide a surgical stapler wherein each of the first and second forming blocks include a facing surface shaped and dimensioned to engage the staple during the bending procedure.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a sectional, side view of the distal end of the low profile surgical stapler showing a first embodiment for a staple deploying assembly prior to the deployment of a staple.

FIG. 3 is an isolated, isometric view of a staple in a pre-firing form.

FIG. 4 is a sectional, side view of the distal end of the low profile surgical stapler showing the forming and deployment of a staple.

FIGS. 5A and 5B are respectively a cross sectional views of the connection between the shaft and the staple deploying assembly.

FIG. 6 is a cross sectional side view showing the connection between the shaft and staple deploying assembly.

FIGS. 7A and 7B are respectively a rear view and a side view of alternate embodiment showing the connection between the shaft/staple deploying assembly and the handle assembly.

FIG. 8 is a side view of an exemplary low profile surgical stapler in accordance with an alternate embodiment.

FIG. 9 is an isometric view of the distal end of a low profile surgical stapler as shown in FIG. 8 showing a second embodiment of a staple deploying assembly prior to staple deployment.

FIG. 10 is a side sectional view of the second embodiment shown in FIG. 8, with the stapler shaft removed.

FIG. 11 is an isometric, partial view of the second staple deploying embodiment, showing a staple and staple drivers in a fully deployed position.

FIG. 12 is an isometric view of the distal end of a low profile surgical stapler showing the staple in a deployed position prior to release.

FIG. 20 is a side view of a second exemplary low profile surgical stapler showing an open distal shaft tip.

FIG. 21A is a side sectional view of the distal end of the stapler shaft showing a third staple deploying assembly embodiment prior to deployment.

FIG. 21B is a top sectional view of the distal end of the stapler shaft showing the third staple deploying assembly embodiment prior to deployment.

FIGS. 36A-36H depict the firing sequence for a fourth staple deploying assembly embodiment.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 4, a surgical stapler 10 for delivering fasteners 12 to a tissue site, for example, a gastric site during gastric reduction surgery, is disclosed. The various embodiments disclosed in the present application relate to the provision of a low-profile surgical stapler 10 that enables a large-sized fastener or staple 12 to be delivered into a body cavity through a small opening or port. As such, it is contemplated the present invention may be utilized in conjunction with either laparoscopic procedures (that is, surgical procedures involving access through a small opening formed in the body, for example, skin access through the use of a trocar) or endoscopic procedures (that is, surgical procedures involving access by passage of a surgical instrument through a natural orifice, for example, transorally)

Figures 22, 23:
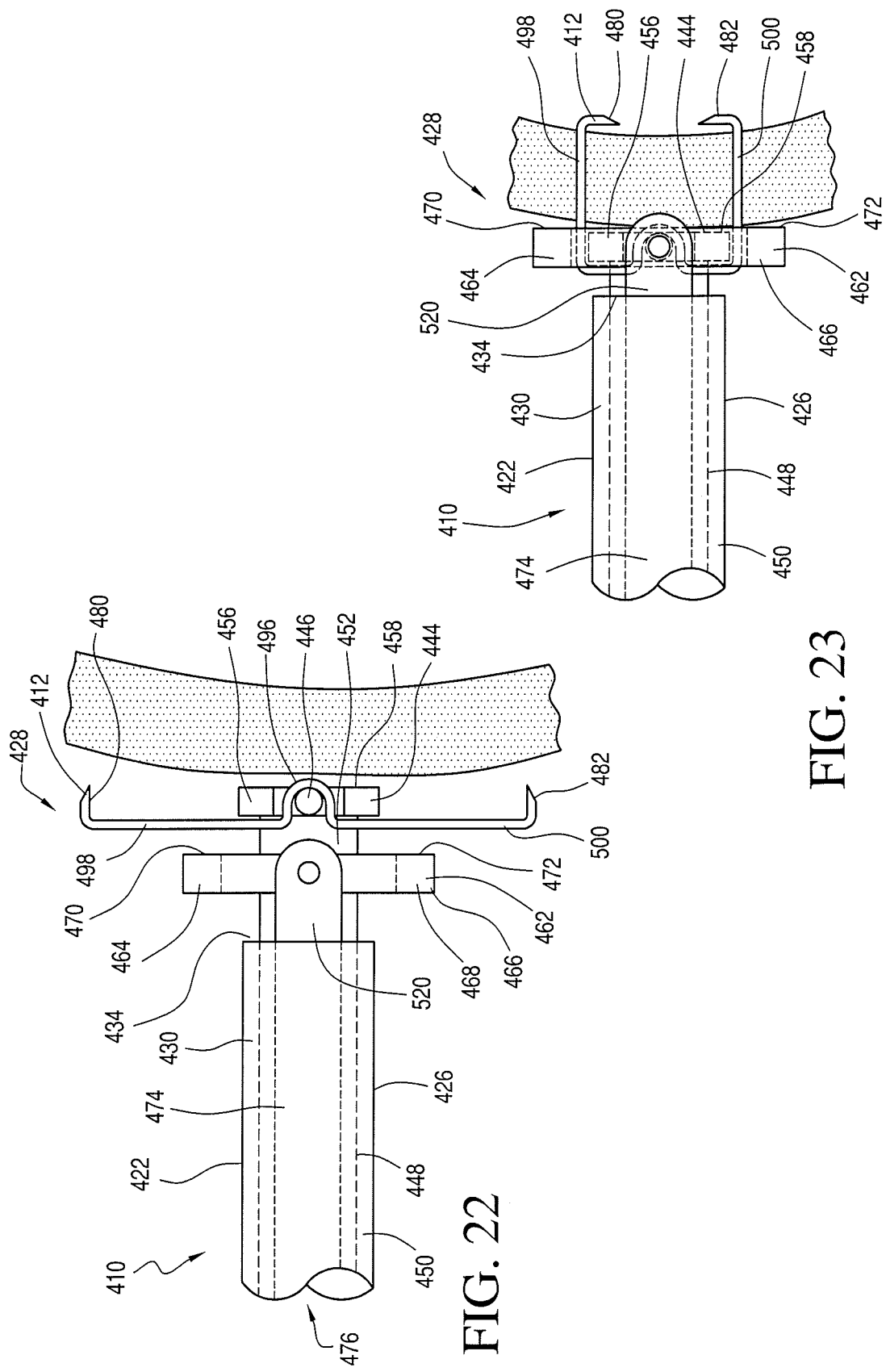
FIG. 22 is a top view of the distal end of the stapler shaft showing the anvil and staple former advanced and rotated 90° during deployment.
FIG. 23 is a top view of the distal end of the stapler shaft showing a staple being deployed into multiple tissue layers.
Figure 24:
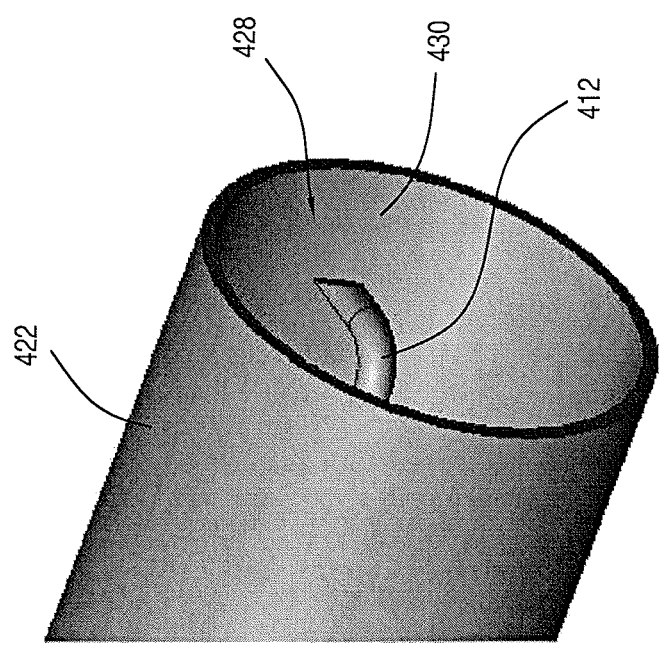
FIGS. 24 to 35 shows the steps associated with use of the surgical stapler disclosed with reference to FIGS. 20-33.
Figure 25:
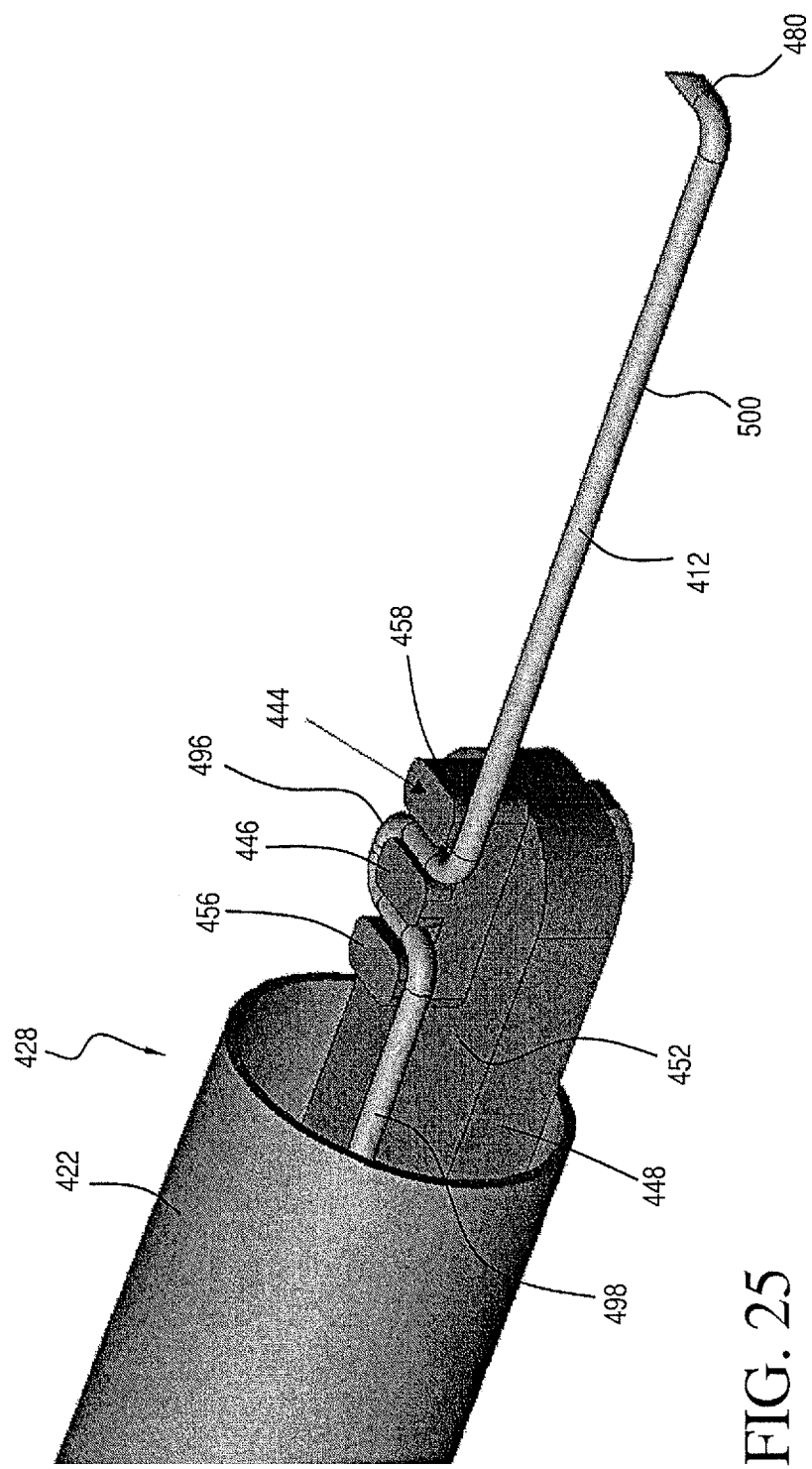
Figure 26:
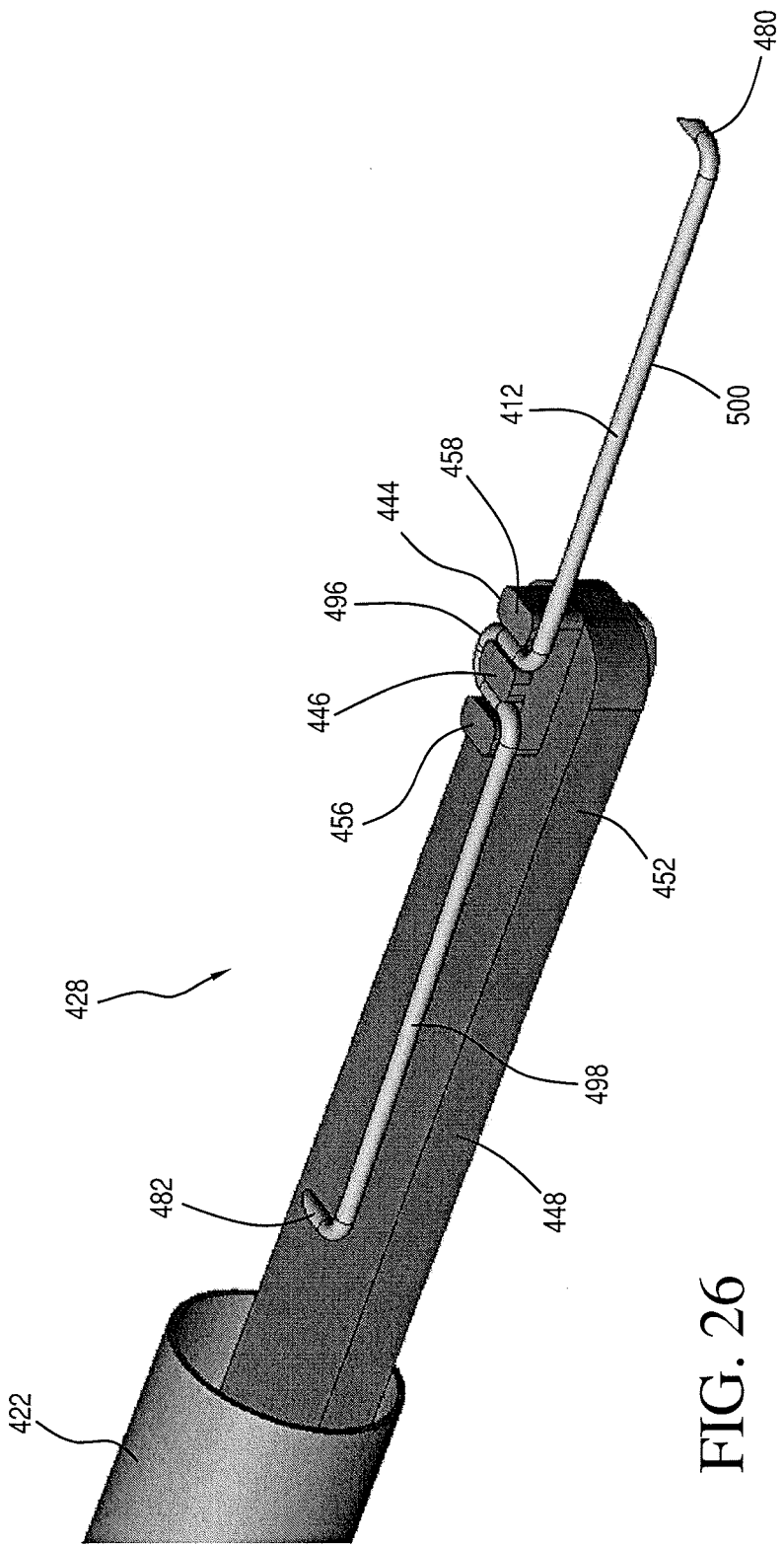
Figure 27:
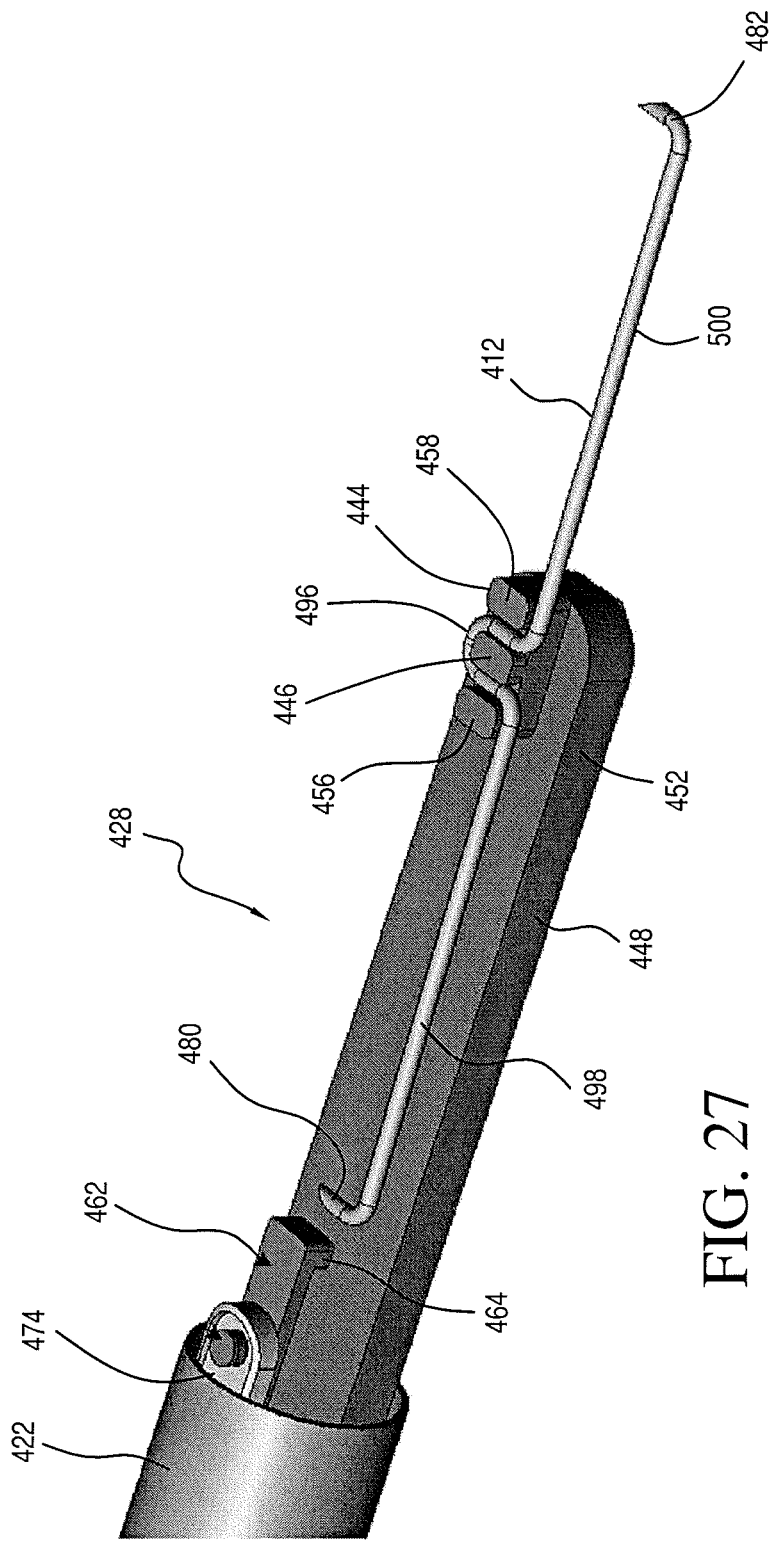
Figure 28:
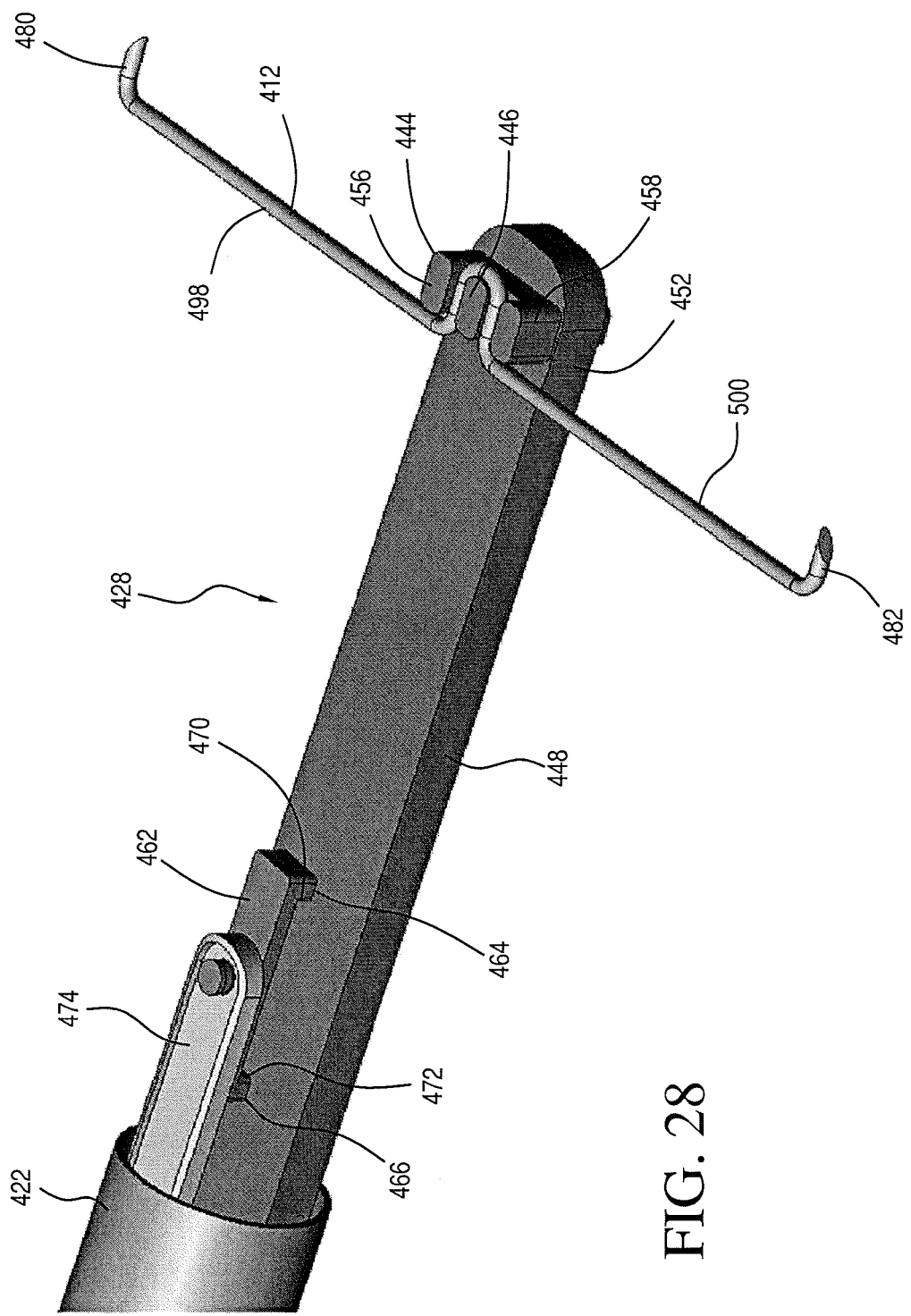
Figure 29:
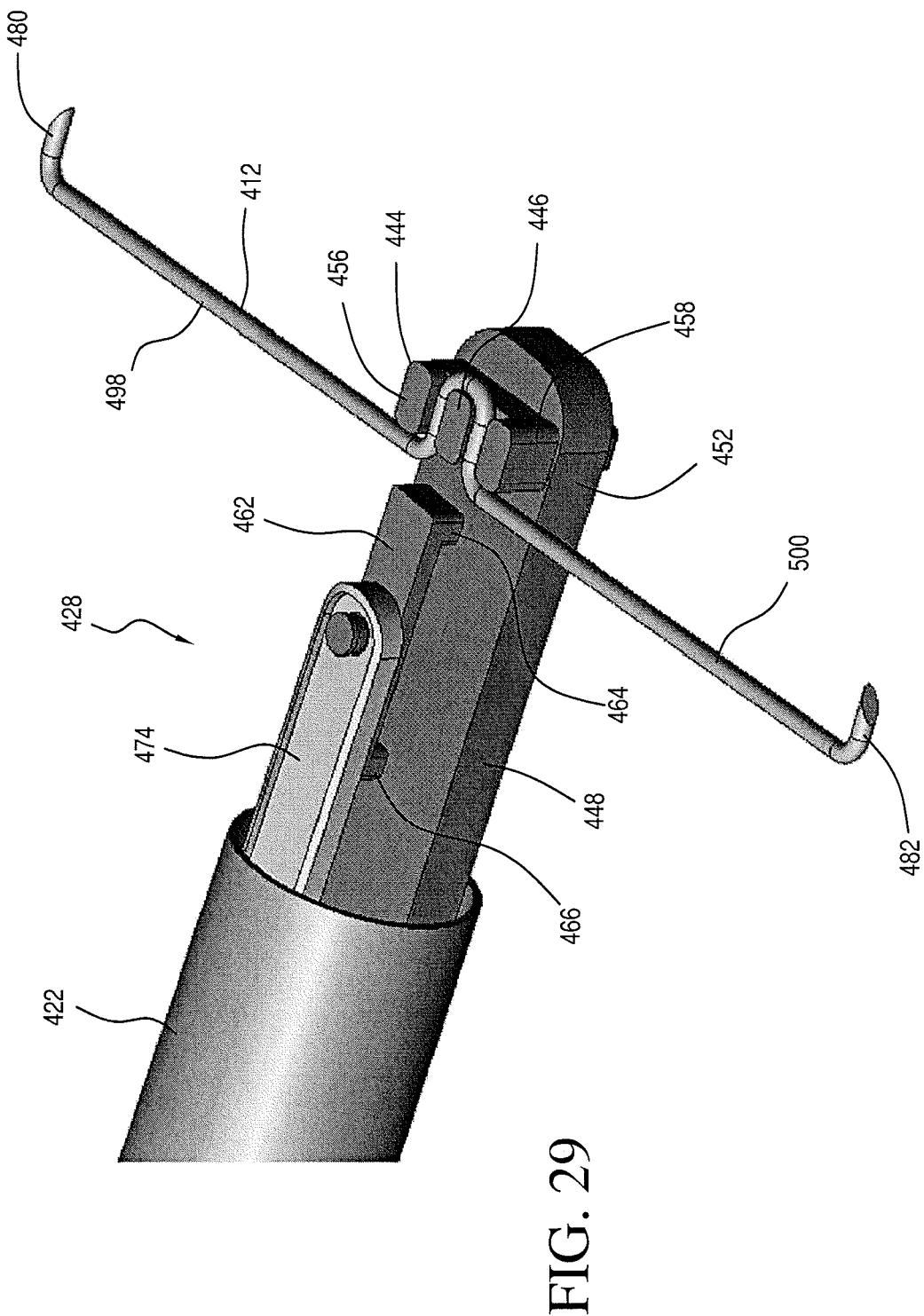
Figure 30:
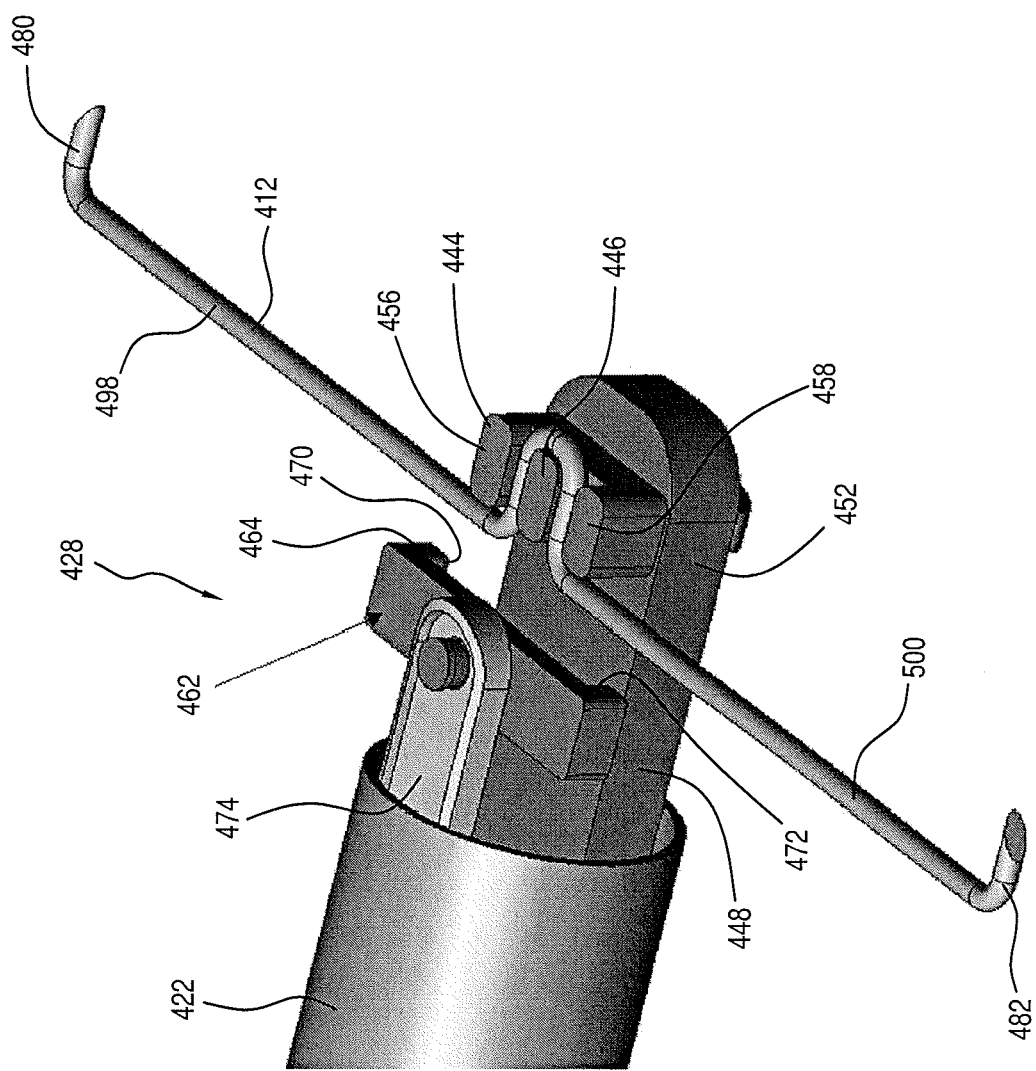
Figure 31:
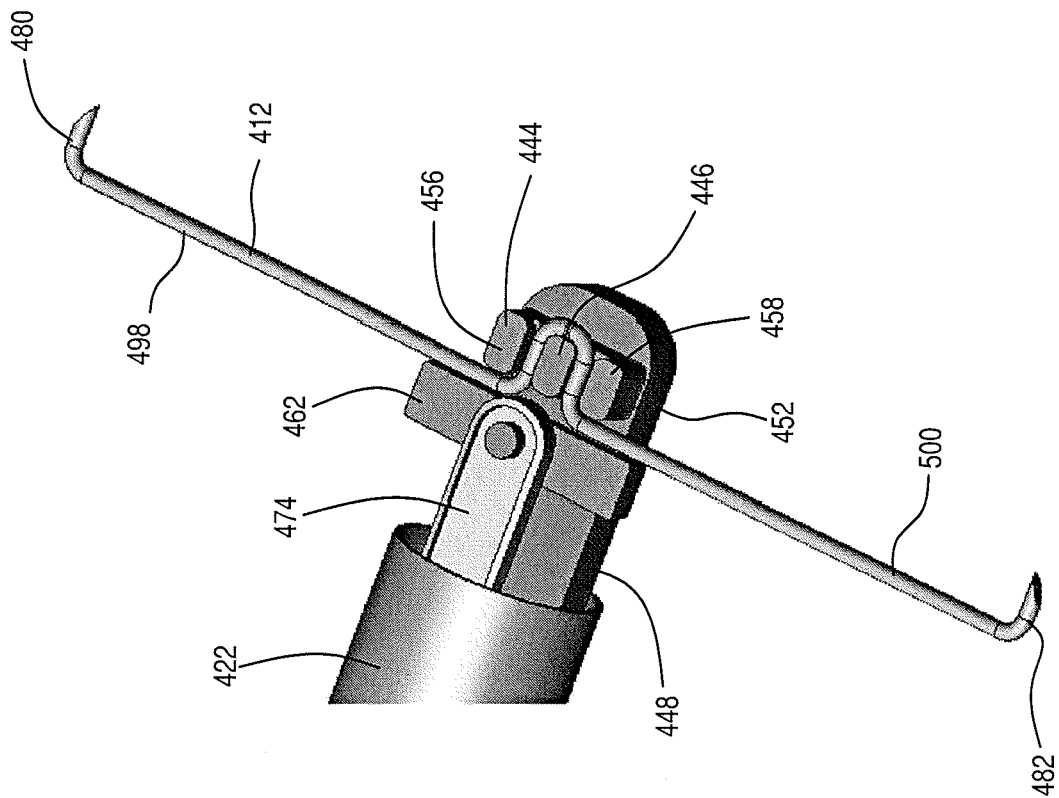
Figure 32:
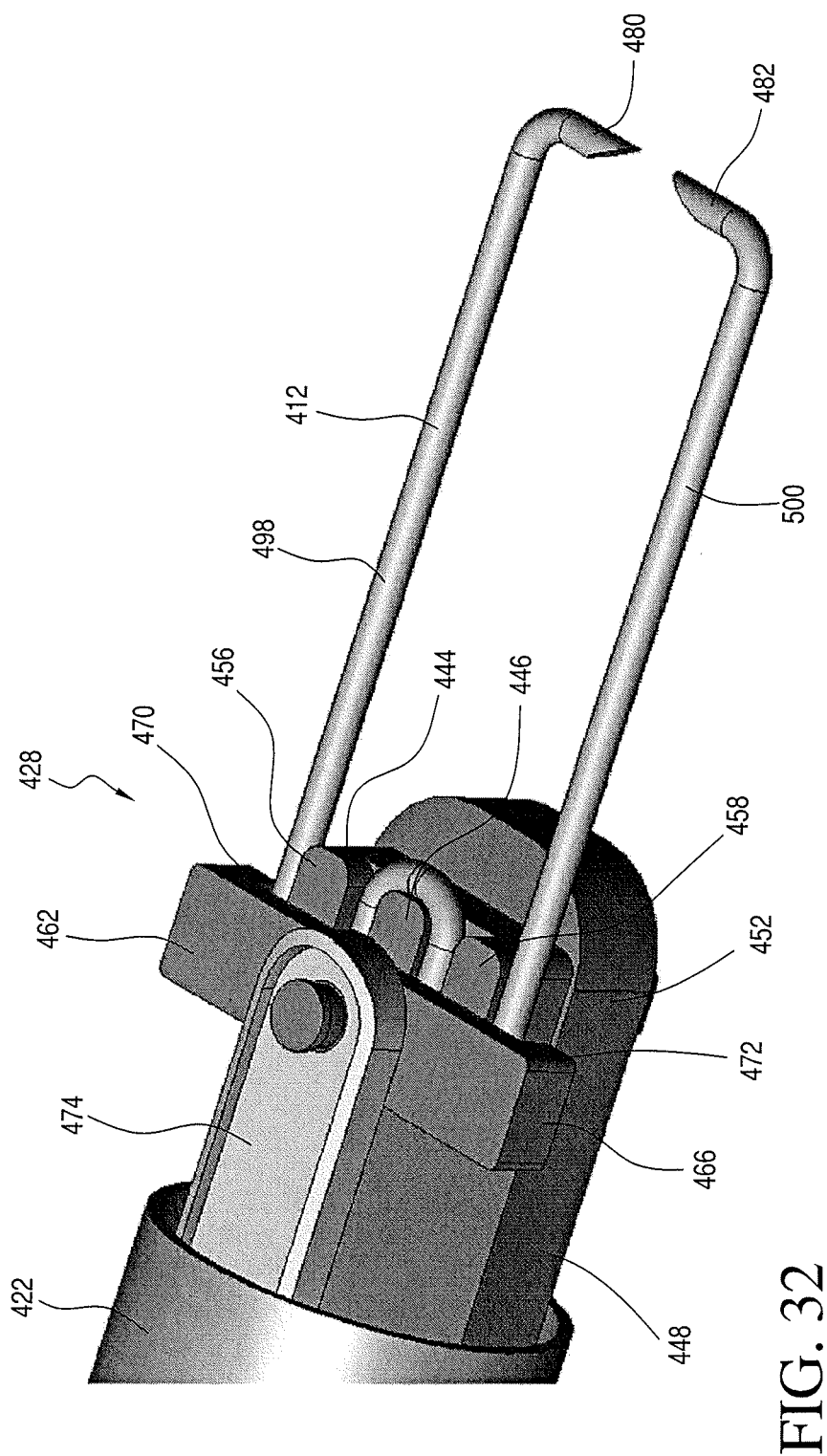
Figure 33:
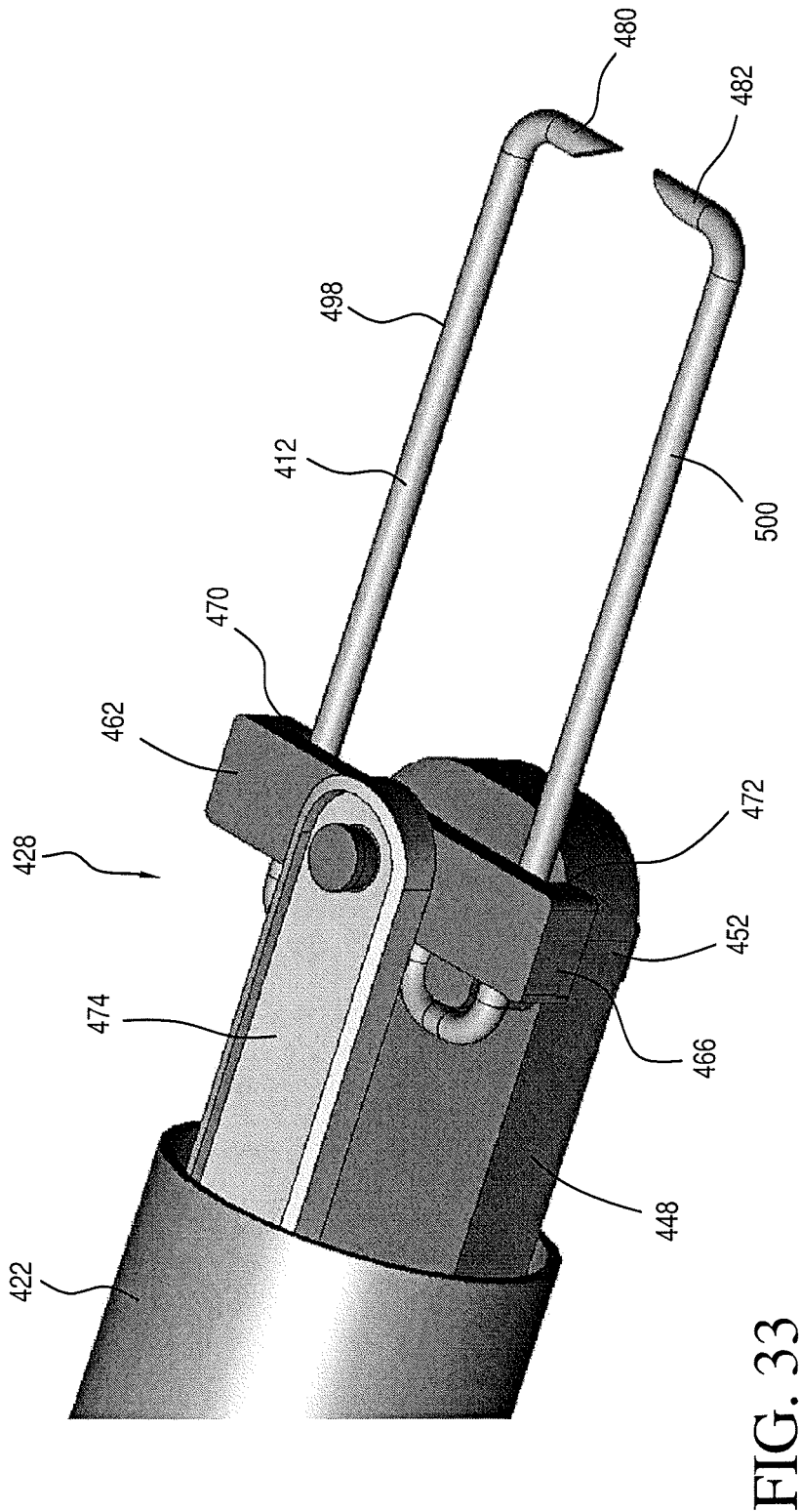
Figure 34:
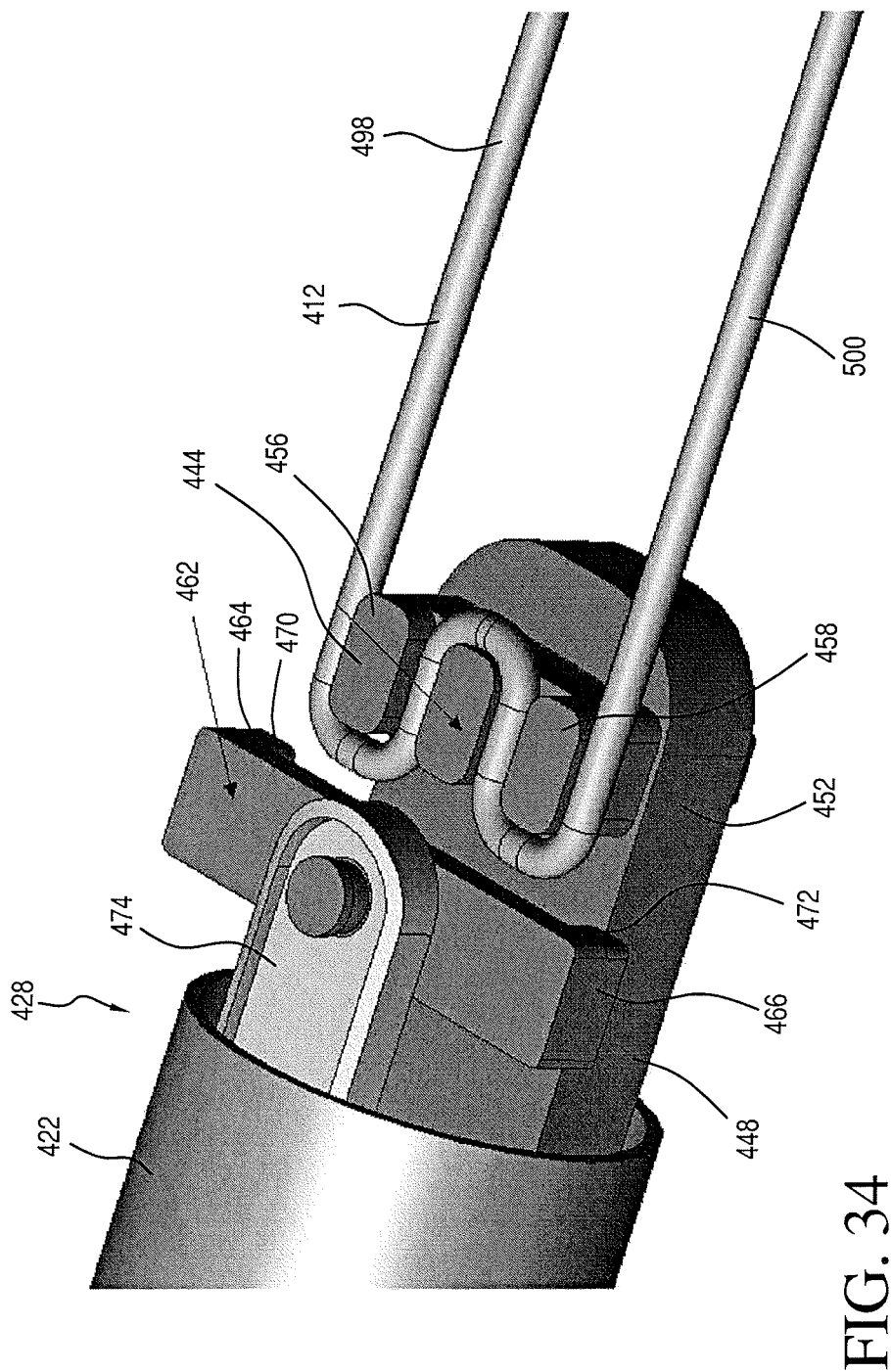
Figure 35:
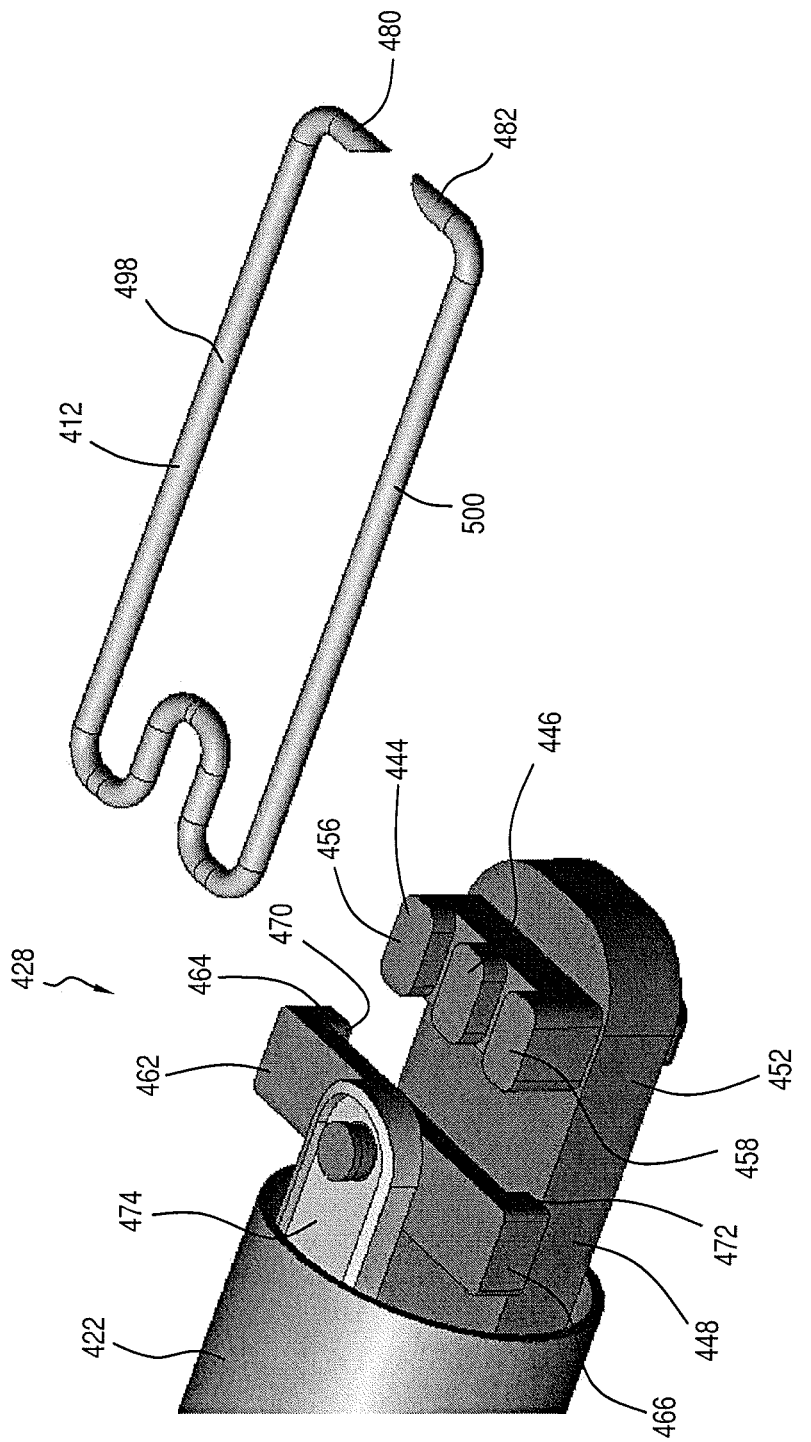

The term "large-sized" is intended to refer to staples or fasteners that are much bigger than the size of a trocar port or natural body orifice used in accessing the surgical site. If one looks at FIG. 12, the legs 98, 100 of the staple 12 are longer than the diameter of the shaft 22 of the surgical stapler 10. FIG. 22 also shows how the width of the staple 12 is wider than the shaft 422 of the stapler 410 that it came out of. As a result of the present invention, one is able to deliver a staple having a length dimensioned bigger than the diameter of the delivery port or natural body orifice (in prior staplers or other fastener delivery devices, the size of the staple or fastener determines the trocar port size). An open skin stapler device uses a large sized fastener, and would be considered to be much to big to fit down a 5 mm trocar port. However, the present invention allows a staple of approximately the same size as used in conjunction with an open skin stapler device to be delivered down a 5 mm trocar port. As far as industry standards on staple sizes, there are many sizes used is surgery today. A skin stapler uses approximately 0.56 mm wire diameter while an internal cutting stapler uses wire diameter's as small as approximately 0.17 mm wire diameter. The staple crown width on the skin stapler is 6 mm while the internal cutting stapler uses a crown width of approximately 2.5 mm. The concept of the present invention, as will be discussed below in greater detail, is to use the large sized staple, like in the skin stapler, inside the body cavity and delivered through a trocar port or natural body orifice smaller than the staple itself, for example a 5 mm trocar.

The distal, deploying end 14 of the surgical stapler 10 is sized to pass through a small (for example, 5 mm) trocar port or a flexible endoscope during a minimally invasive surgical procedure. The present low profile surgical stapler 10 enables larger areas of tissue to be joined together inside a body cavity through a small access port. Inside the body cavity, the surgical stapler 10 can be deployed to secure multiple layers of tissue together, for example, in a manner reducing the effective volume of the gastric cavity during gastric reduction surgery. Although the present surgical stapler 10 is disclosed herein for use in the performance of gastric reduction surgery, the present surgical stapler 10 may be used in performing a variety of surgical procedures without departing from the spirit of the present invention.

Figure 1:
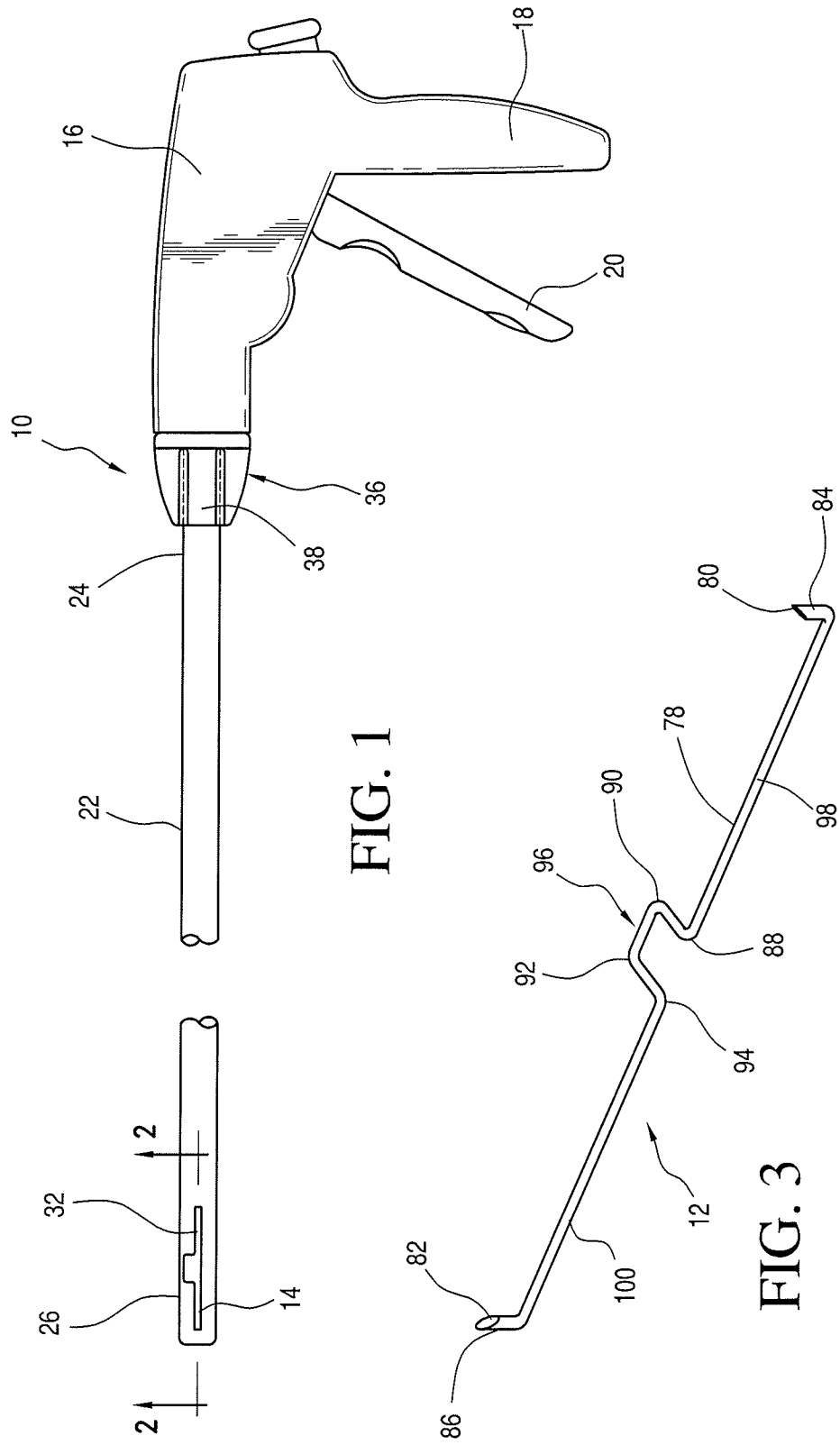
FIG. 1 is a side view of an exemplary low profile surgical stapler.
Figure 13:
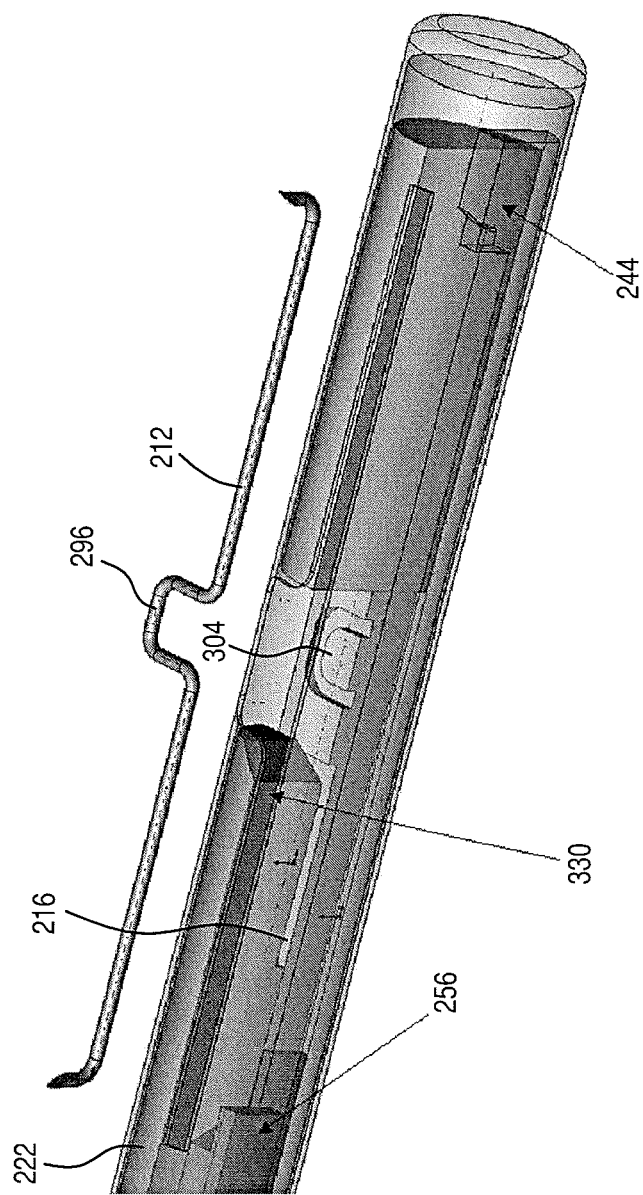
FIGS. 13 to 19 show the various steps in deployment of the staple in accordance with the embodiment disclosed with reference to FIGS. 1 to 7.
Figure 14:
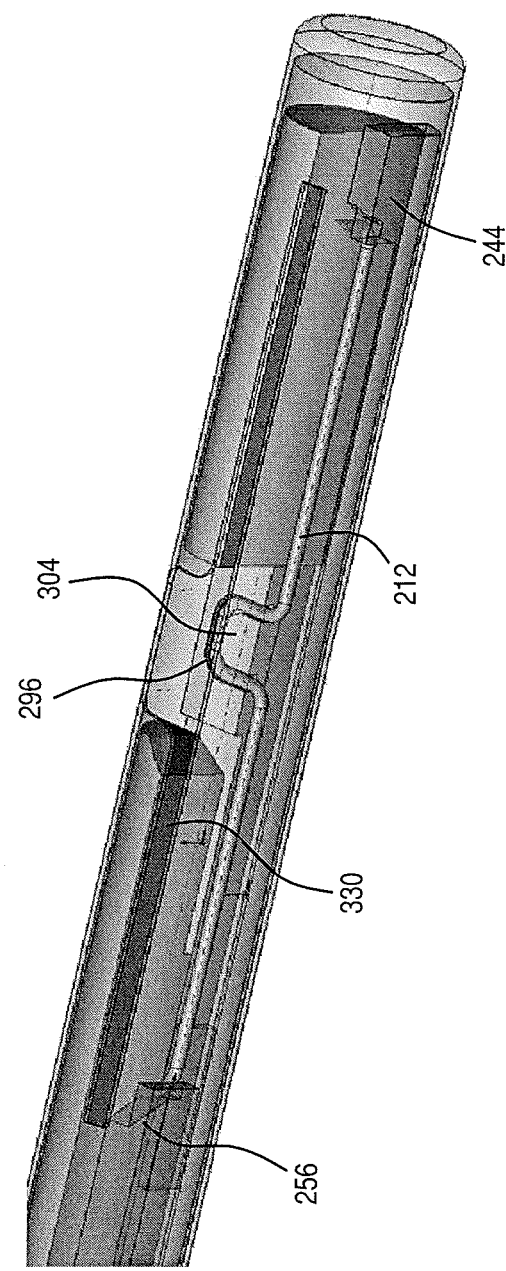
Figure 15:
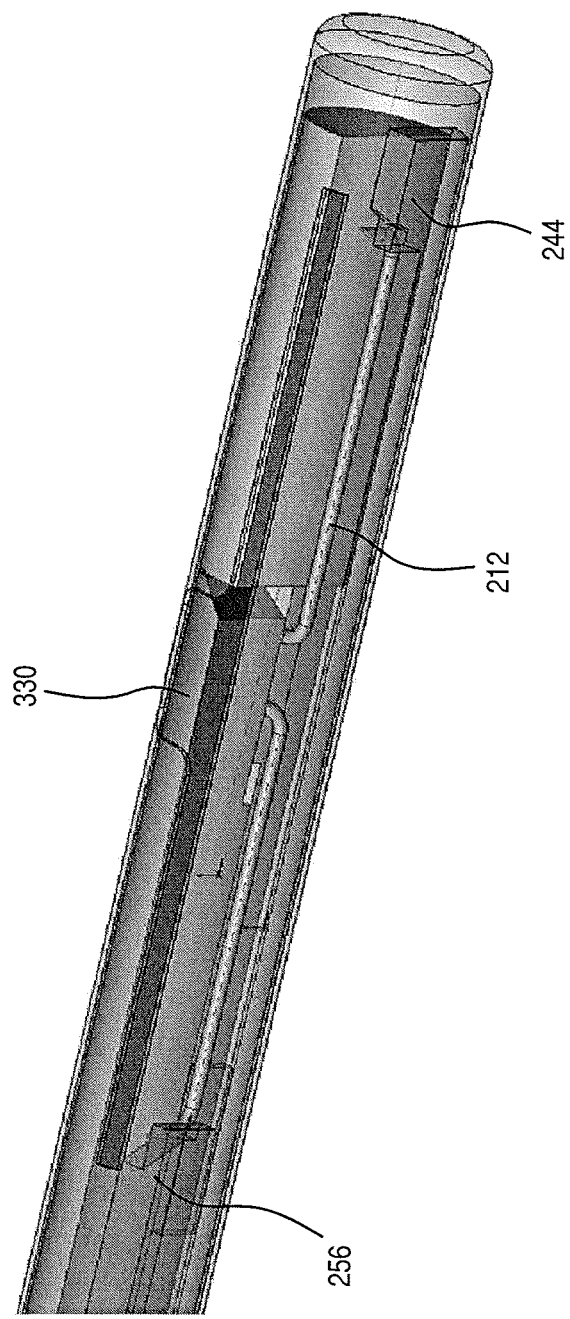
Figure 16:
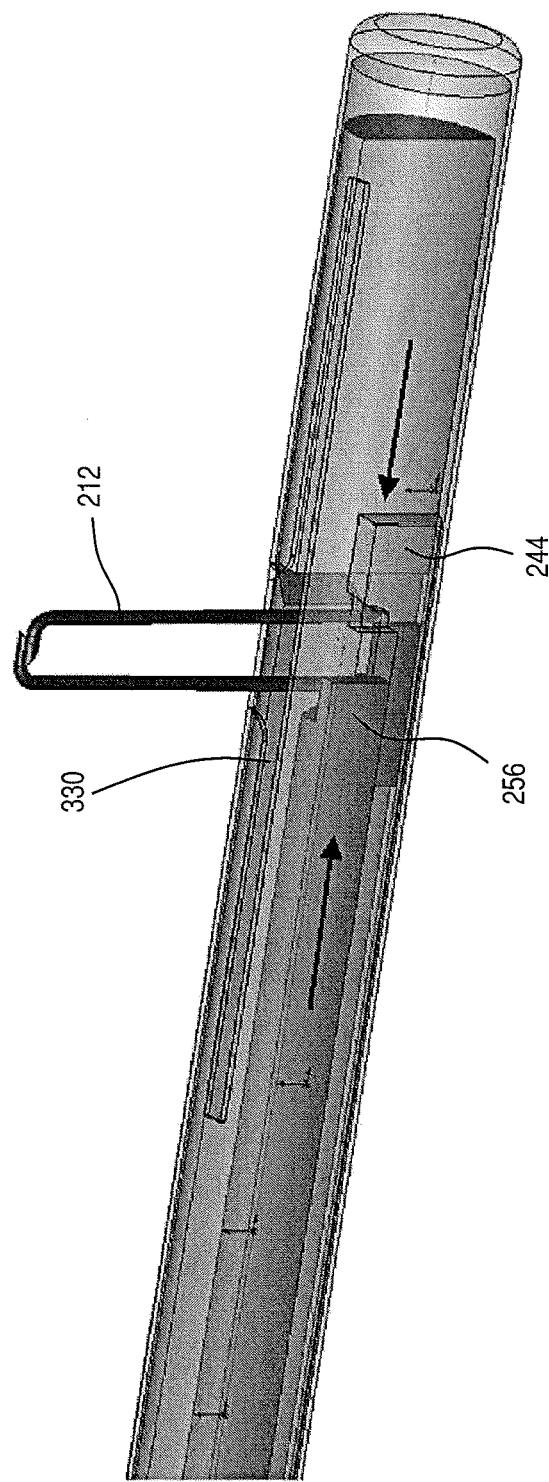
Figure 17:
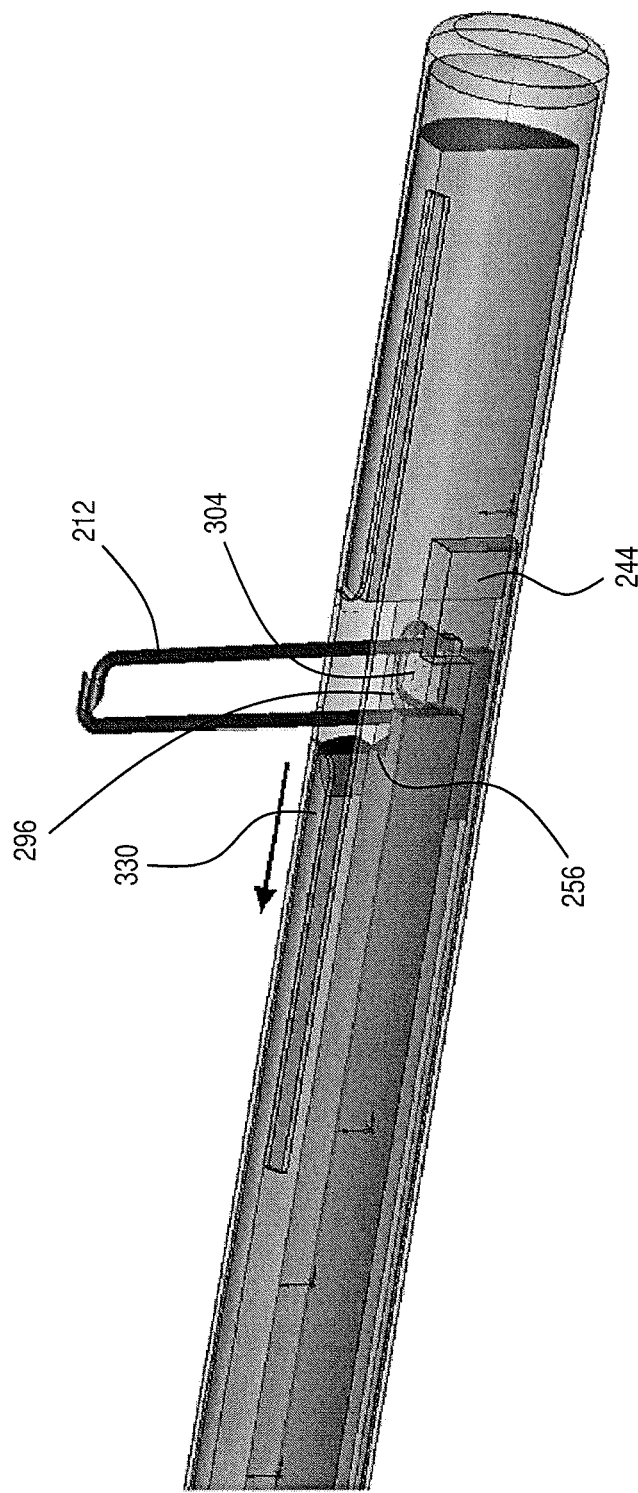
Figure 18:
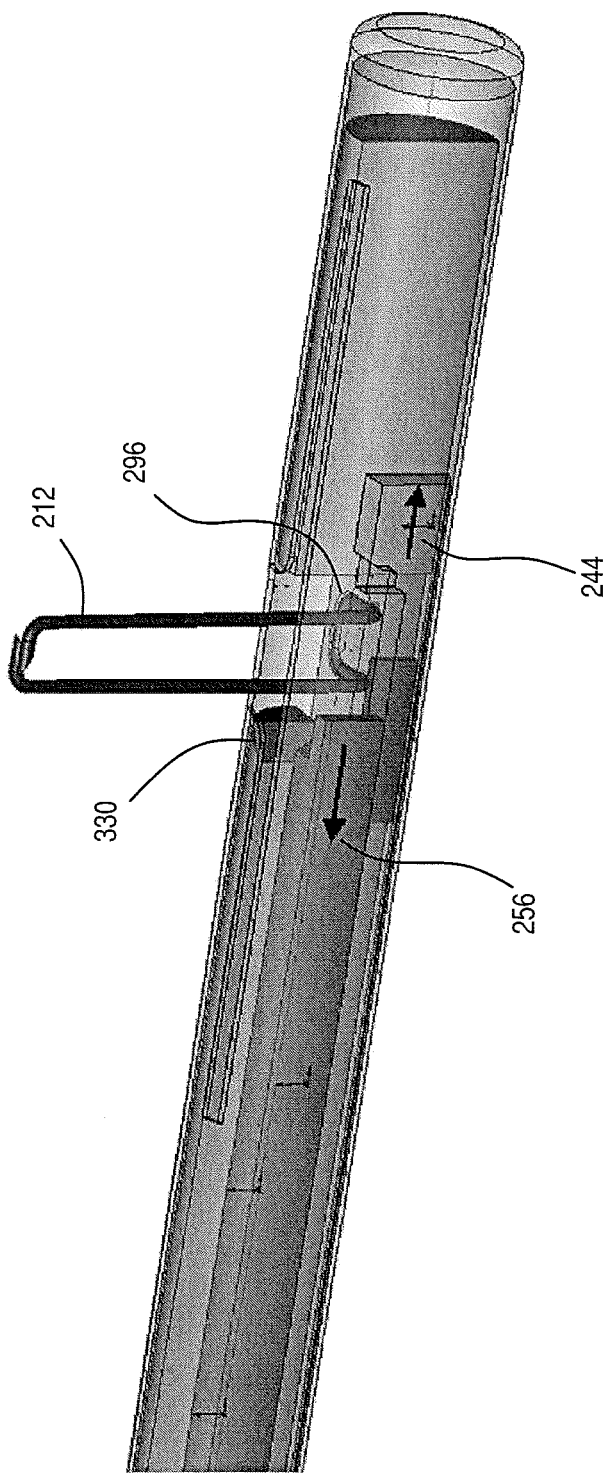
Figure 19:
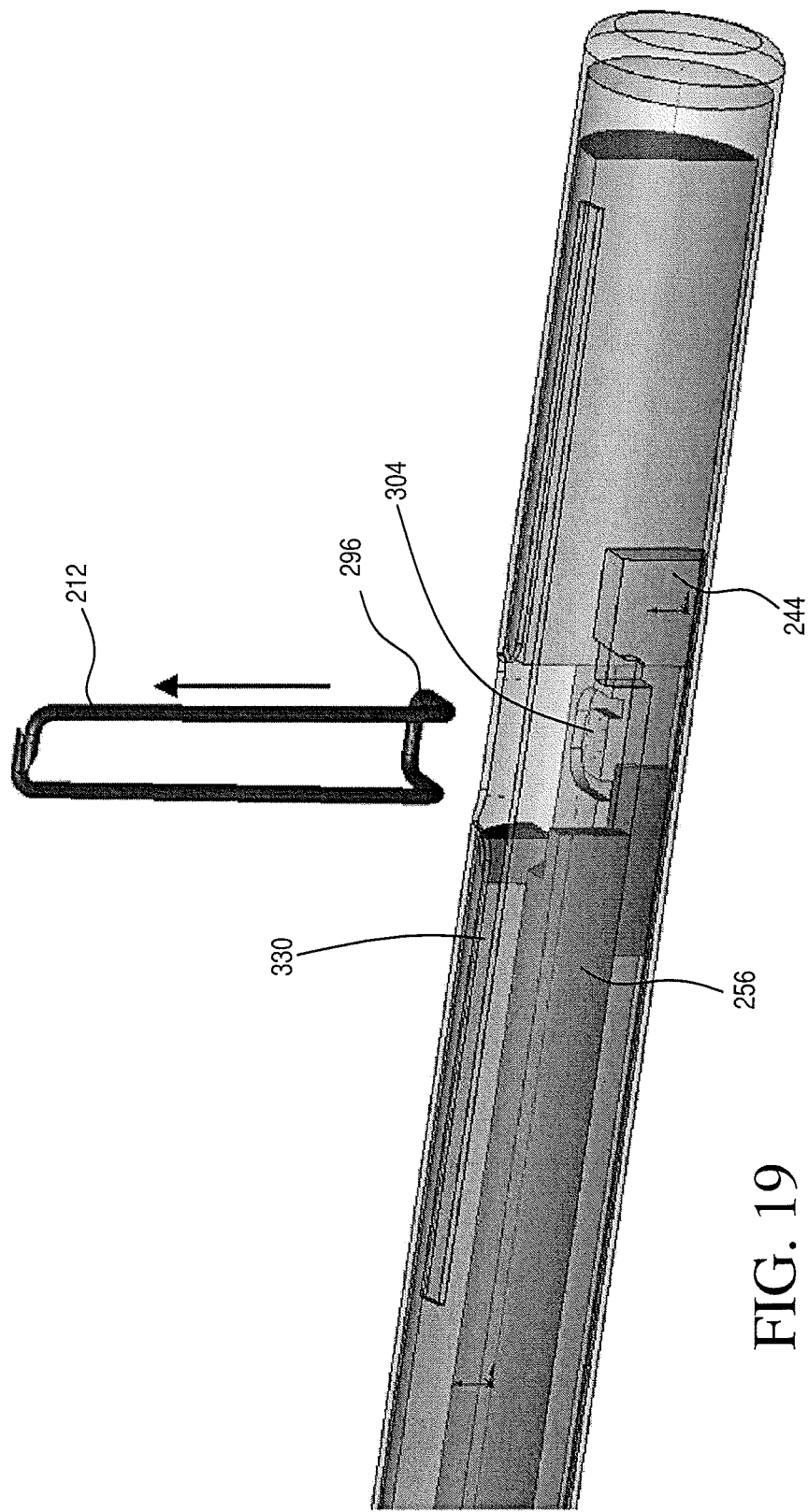

FIGS. 1, 2 and 4 show a low profile surgical stapler 10 for discharging large staples 12 into multiple tissue layers in accordance with a preferred embodiment of the present invention. The surgical stapler 10 includes a handle 16 having a pistol grip 18 shaped for gripping by a surgeon. A trigger 20 is movably coupled to the handle 16 to be drawn toward the pistol grip 18 during staple deployment. An elongated, tubular shaft 22 extends distally from the handle 16. The tubular shaft 22 includes a proximal end 24 secured to the handle 16 and a distal end 26 from which staples 12 are deployed in accordance with the present invention and as discussed below in greater detail.

A staple deploying assembly 28 is disposed within the interior 30 of the shaft 22 for discharging staples 12 from the distal end 14 of the surgical stapler 10. As will be appreciated based upon the following disclosure, the staple deploying assembly 28 supports a staple 12 such that a longitudinal axis of the staple 12 is aligned with a longitudinal axis of the shaft 22, thereby allowing for deployment of large-sized staples 12 as described above. More particularly, the shaft 22 includes a lateral, deployment opening 32 at the distal end 26 of the shaft 22 and extends through the side of the shaft 22 adjacent a closed, distal tip 34 thereof. The deployment opening 32 is elongated in the direction of the longitudinal axis of the shaft and is, therefore, shaped and dimensioned to permit the deployment of the staples 12 from within the shaft 22, out of the deployment opening 32 and into adjacent tissue.

In accordance with a preferred embodiment, the shaft 22 has a diameter that is less than approximately 5 mm to allow for insertion of the shaft 22 through a cannula or trocar (not shown) during an endoscopic or laparoscopic surgical procedure. As will be appreciated based upon the following disclosure, the trigger 20 facilitates both the advancement of a staple 12 through the shaft 22, as well as the deployment of the surgical stapler 10 from the distal end 26 of the shaft 22. In accordance with an alternate embodiment, it is contemplated separate triggers or activating mechanisms may be incorporated into the surgical stapler for conveying a staple through the shaft and deploying the staple externally from the shaft and through the deployment opening into adjacent tissue.

In a surgical application, the surgical stapler 10 is manipulated through a trocar or endoscope to a desired location where the deployment opening 32 along the distal end 26 of the shaft 22 is pushed against the tissue area to be fastened. To facilitate placement of the deployment opening 32 against a selected tissue area, the shaft 22 is rotatably secured to the handle 16 and a rotating knob 36 is provided on the handle 16. The rotating knob 36 includes a centralized bore 38 through which the shaft 22 extends. A boss (not shown) in the interior of the knob bore 38 engages a notch or slot (not shown) on the exterior surface (not shown) of the shaft 22. As the knob 36 is rotated, the shaft 22 is in turn rotated by the interaction of the knob boss with the shaft 22. As the shaft 22 rotates, the location of the deployment opening 32 changes circumferentially relative to the surrounding tissue, thereby repositioning the deployment opening 32 against different areas of tissue. It will be appreciated that a connection also exists between the rotating knob 36 and the staple deploying assembly 28 inside of the shaft 22, so that rotation of the knob 36 also produces rotation of the staple deploying assembly 28 about the longitudinal axis of the shaft 22.

Referring to FIGS. 5A, 5B, 6, 7A and 7B, a mechanism is disclosed for utilizing the rotating knob 36 to turn the staple deploying assembly 28 as the shaft 22 is similarly rotated without turning the handle 16 at the proximal end of the surgical stapler 10. In accordance with a preferred embodiment of the present invention, the firing of the staple 12 is accomplished with either a push or pull motion down the axis of the shaft 22 as the trigger 20 acts upon the staple deploying assembly 28. This linear motion is connected to a trigger 20 to generate enough leverage to form the staple 12 as described below in greater detail. Between the trigger 20 and the rotating portion of the staple deploying assembly 28 this motion must be allowed to rotate so that the rotation does not require a user to turn his or her wrist to align the deployment opening 32 of the staple deploying assembly 28 to the tissue.

In accordance with a preferred embodiment, and with reference to FIGS. 5A and 5B, a snap ring 118 is used to link the distal end of the shaft 22 to the staple deploying assembly 28, in particular, an attachment post 120 extending from a proximal end of the staple deploying assembly 28. The snap ring 118 includes projections 122 for engaging elongated recesses 124 along the attachment post 120 ensuring that rotation of the shaft 22 will cause rotation of the attachment post 120 in a manner desired by users of the present surgical stapler 10, while also allowing linear movement of the attachment post 120 for transferring the linear motion of the trigger 20 to the staple deploying assembly. In accordance with an alternate embodiment as shown with reference to FIG. 6, a set screw 126 is used to link the shaft 22 to the attachment post 120 in a manner facilitating rotation in accordance with the present invention, while also allowing linear movement of the attachment post 120 for transferring the linear motion of the trigger 20 to the staple deploying assembly. Whether a snap ring 118 or a set screw 126 is used, the shaft 22 is secured to the trigger 20 via a yoke 128 that allows rotation of the shaft 22 relative to the trigger 20, while also permitting linear movement of the attachment post 120 as the trigger 20 is actuated to form a staple 12 in accordance with the present invention (see FIGS. 7A and 7B).

FIGS. 2 and 4 illustrate the distal portion of the shaft 22 wherein a staple deploying assembly 28 in accordance with a first embodiment is shown. In accordance with this embodiment, a first staple driver 44 extends longitudinally through the interior 30 of the shaft 22. The first staple driver 44 includes a proximal end 46 and a distal end 48. The proximal end 46 of the first staple driver 44 is attached to a driving assembly, that is, the attachment post 120 that is directly actuated via the trigger 20 (as shown with reference to FIGS. 5A, 5B, 6, 7A and 7B, and as discussed above) as indicated by an arrow. Briefly, and as discussed above, this connection allows the shaft 22 to turn with the rotation knob 36 for adjusting the orientation of the staple deploying assembly 28 and the deployment opening 32 while allowing for linear movement of the first and second staple drivers 44, 56 under the control of the trigger 20. The handle of the surgical stapler does not turn.

The driving assembly is actuated by the trigger 20 for controlled fastening of staples 12 to desired tissue locations in a manner discussed below in greater detail. The distal end 48 of the first staple driver 44 includes a proximally facing camming surface 50 that is shaped at an angle relative to the longitudinal axis of the first staple driver 44. In addition, the distal end wall 52 of the first staple driver 44 includes an angled surface that is shaped at an angle relative to the longitudinal axis of the first staple driver 44. The angle at which the distal end wall 52 is oriented coincides with the angled interior surface 54 at the distal tip 34 of the shaft 22 such that the distal end wall 52 of the first staple driver 44 is housed within the distal tip 34 of the shaft 22 prior to firing. The distal tip 34 of the shaft 22 serves to contain the distal end 48 of first staple driver 44 within the shaft 22.

A second staple driver 56 also extends from the driving assembly (not shown), distally through the shaft 22, to a point just proximal of the deployment opening 32. The second stapler driver 56 also includes a proximal end 58 connected to the driving assembly and a distal end 60. The second staple driver 56 is controlled by the driving assembly so as to be propelled distally along the longitudinal axis of the shaft 22 during folding and deployment of a staple 12 in accordance with the present invention. The distal end 60 of the second staple driver 56 includes a distally facing camming surface 62 that is shaped at an angle relative to the longitudinal axis of the second staple driver 56.

First and second bending arms 64, 66 are longitudinally disposed in the interior 30 of the shaft 22. The first and second bending arms 64, 66 are oriented in a manner facing the deployment opening 32 such that a staple 12 may be supported thereon during folding and subsequent ejection from the deployment opening 32. The first and second bending arms 64, 66 are joined together at a pivot point 68 so as to rotate towards each other in the direction of the deployment opening 32. A pin 70 extends from the pivot point 68 to the interior wall 72 of the shaft 22 to affix the pivot point 68 of the first and second bending arms 64, 66 to the shaft 22, and thereby prevent the first and second bending arms 64, 66 from sliding longitudinally within the shaft 22 of the surgical stapler 10 during deployment. Opposing free ends of the respective first and second bending arms 64, 66 include a tapered edge 74, 76 extending in a direction away from the deployment opening 32. As mentioned above, the first and second staple drivers 44, 56 respectively include camming surfaces 50, 62 that face the tapered edges 74, 76 of the first and second bending arms 64, 66. The slope of the camming surfaces 50, 62 of the first and second staple drivers 44, 56 is the same as the tapered edges 74, 76 of the first and second bending arms 64, 66, so that the free ends of the bending arms 64, 66 make sliding contact with the camming surfaces 50, 62 of the first and second staple drivers 44, 56 during firing.

To fire the present surgical stapler 10, a staple 12 is first conveyed through the shaft 22 into a deployment position opposite the deployment opening 32. A staple 12 is conveyed with the length of the staple 12 lying along the longitudinal axis of the shaft 22. In accordance with a preferred embodiment, the staple 12 is conveyed down the shaft 22 by a series of latching shuttle movements. A preferred shuttle movement for use in accordance with the present invention is employed in a laparoscopic clip applier, for example, see U.S. Pat. No. 4,430,997 (Please see FIG. 4a, 4b, 5a, 5b, 6a, 6b), which is incorporated herein by reference. The '997 patent describes a mechanism for providing a reciprocating motion for feeding clips (in accordance with the present surgical stapler) in succession. A top support and bottom support are required, each of these long bars have teeth or ramps that allow the staple to feed only distally. As either the top or bottom is reciprocating the staples are pushed one full stroke with each reciprocating movement. The entire stack of staples can be advanced together in this way.

Individual staples 12 may be loaded into the surgical stapler 10 and advanced through the shaft 22. Alternatively, a staple cartridge (not shown) may be preloaded into the surgical stapler 10 and the staples 12 individually moved from the cartridge to the deployment opening 32 each time the surgical stapler 10 is fired. FIG. 3 is an isolated view of a staple 12 showing the initial, pre-fired structure of the staple 12 in greater detail. As shown in FIG. 3, a staple 12 includes a long body segment 78 having a longitudinal axis. First and second prongs 80, 82 are found at opposite ends of the body segment 78 and extend in a direction that is substantially transverse to the longitudinal axis of the body segment 78. The first and second prongs 80, 82 extend in substantially the same direction. In accordance with a preferred embodiment, the first and second prongs 80, 82 are preferably bent at a 90° angle from the body segment 78 to facilitate entry of the staple 12 into tissue during firing. Each of the first and second prongs 80, 82 includes sharpened end points 84, 86 for piercing the tissue.

A series of four approximately 90° bends 88, 90, 92, 94 are formed in the midsection of the body segment 78. These bends 88, 90, 92, 94 within the body segment 78 form a "box" area 96 at the center of the staple 12. The bends 88, 90, 92, 94 are formed in the body segment 78 such that the plane of the box 96 is perpendicular to the plane in which the first and second prongs 80, 82 lie. The box 96 divides the body segment 78 into a pair of legs 98, 100. The box 96 facilitates the advancement of a staple 12 through the shaft 22 into the deployment position opposite the deployment opening 32. Additionally, the box 96 provides control over a staple 12 as the staple 12 is shaped during deployment.

As shown in FIGS. 2 and 4, the end effector 102 of the present surgical stapler 10 includes a support post 104 moveable for positioning adjacent the deployment opening 32 and in alignment with the first and second bending arms 64, 66. It is contemplated in certain configurations the post can be fixed within the shaft and staples could be shuttled down and over the post for deployment. The support post 104 supports the staple 12 at the box 96 as the staple 12 is conveyed and bent during deployment. The support post 104 has a rectangular shape which mates with the similarly shaped box 96 of the staple 12. In particular, the support post 104 includes four upwardly extending sidewalls 106, 108, 110, 112 and is shaped to sit within the spaced defined by the box 96 formed along the central portion of the body segment 78. The fit between the support post 104 and the box 96 is tight enough to maintain the staple 12 in a fixed position during conveying and bending, yet not so secure that the staple 12 cannot be released from the support post 104 after bending. In accordance with a preferred embodiment, the support post 104 is formed on the distal end 114 of a pushrod 116 that is driven longitudinally through the shaft 22 between a staple cartridge (not shown) and the deployment opening 32.

Referring to FIGS. 13-19 a mechanism for staple deployment is disclosed below with reference to the embodiment disclosed in FIGS. 8-12, and is considered appropriate for use in conjunction with this embodiment although not repeated herein. Briefly, a locking bar slides over the support post and staple to lock the staple in place prior to firing. The locking bar holds the central portion along the body segment of the staple in place during firing. The locking bar is pulled back just after firing prior to disengagement from tissue.

In the event a cartridge design is employed, a shuttle advancing mechanism design would be used to shuttle staples from within the proximal shaft to the firing position. At the firing position they would be shifted out of the delivery plane downward around and into the box 96.

In an initial deployment step, a staple 12 is moved onto the support post 104 and the staple 12 is transferred longitudinally through the shaft 22 by moving the support post 104 under the control of the pushrod 116 to a position just inside of the deployment opening 32. While the staple 12 is transferred through the shaft 22 by moving the support post 104 in accordance with a preferred embodiment of the present invention, it is contemplated the staple 12 may be brought directly to the support post 104. The staple 12 is positioned with the box 96 in a plane parallel to the deployment opening 32 with the first and second prongs 80, 82 extending perpendicular to the box 96 in the direction of the deployment opening 32. In this position, the first and second prongs 80, 82 are poised to enter tissue adjacent the deployment opening 32 at a normal angle as the present surgical stapler 10 is fired.

As the trigger 20 is actuated to deploy a staple 12, a force is applied to the first staple driver 44 to draw the first staple driver 44 proximally within the shaft 22 towards the first bending arm 64. Simultaneously, a force is applied to the second staple driver 56 to propel the second staple driver 56 distally towards the second bending arm 66. As the staple drivers 44, 56 converge within the shaft 22, the camming surfaces 50, 62 of the respective first and second staple drivers 44, 56 engage the corresponding tapered edges 74, 76 of the first and second bending arms 64, 66. The opposing forces of the respective first and second staple drivers 44, 56 simultaneously acting upon the tapered edges 74, 76 of the first and second bending arms 64, 66 pivots the first and second bending arms 64, 66 towards each other in the direction of the deployment opening 32. As the first and second bending arms 64, 66 pivot, the first and second bending arms 64, 66 engage opposite sides of the staple body segment 78 producing a bending action in the staple 12. As the sides of the staple 12 are bent, the box 96 of the staple 12 is firmly held in place by the support post 104 and the locking bar as described above. The support of the support post 104, combined with the inward pivoting action of the first and second bending arms 64, 66, causes the staple 12 to bend at points adjacent to the box 96. The staple 12 bends such that the two sides (or legs) 98, 100 of the body segment 78 swing outwardly through the deployment opening 32, as shown by the dashed lines in FIGS. 2 and 4. By anchoring the midsection of the staple 12 that is, the box 96, and the locking bar as described above during bending, the support post 104 ensures that the sides of the staple 12 are bent adjacent the box 96, rather than at another location along the length of the body segment 78. By holding onto the box 96 during staple formation, the support post 104 and locking bar also prevent the premature release of the staple 12 through the deployment opening 32. The support post 104 and locking bar ensure that the sides of the staple 12 are fully bent into engagement with tissue at the deployment opening 32 prior to release of the staple 12 through the deployment opening 32.

FIG. 4 shows the distal end 26 of the shaft 22 after the camming surfaces 50, 62 of the first and second staple drivers 44, 56 have been fully propelled into engagement with the first and second bending arms 64, 66. As shown in FIGS. 2 and 4, in this position the sides of the staple 12 are fully bent inwardly so that the first and second prongs 80, 82 pierce tissue through the deployment opening 32. After the staple 12 is fully formed and driven into the adjacent tissue, the support post 104 is dislodged from the box 96 to release the staple 12 through the deployment opening 32. Referring to FIGS. 13 to 19, and as discussed above, a locking bar slides over the support post 104 and staple 12 to lock the staple 12 in place prior to firing. The locking bar will hold the central portion of the body segment 78 of the staple 12 in place during firing and the locking bar is pulled back just after firing prior to disengagement from tissue. The support post 104 is dislodged from the staple 12 by pulling the surgical stapler 10 downwardly (and away from the tissue) relative to the fastened tissue, so that the support post 104 is drawn down from inside the box 96. As the staple 12 is released from the surgical stapler 10, the staple 12 is retained within the tissue. Following release of the staple 12, the distal end 14 of the surgical stapler 10 can be redirected to another area of the tissue layers, or the shaft 22 can be rotated via the knob 36 to deploy additional staples 12 into the tissue junction.

FIGS. 8, 9, 10, 11A, 11B and 12 show a distal end 214 of the shaft 222 of a surgical stapler in accordance with an alternate embodiment. As with the prior embodiment as shown with reference to FIGS. 1 to 4, the surgical stapler 210 includes a handle 216 having a pistol grip 218 shaped for gripping by a surgeon. A trigger 220 is movably coupled to the handle 216 to be drawn toward the pistol grip 218 during staple deployment. An elongated, tubular shaft 222 extends distally from the handle 216. The tubular shaft 222 includes a proximal end 224 secured to the handle 216 and a distal end 226 from which staples 212 are deployed in accordance with the present invention and as discussed below in greater detail.

A staple deploying assembly 228 is disposed within the interior 230 of the shaft 222 for discharging staples 212 from the distal end 214 of the surgical stapler 210. More particularly, the shaft 222 includes a lateral, deployment opening 232 at the distal end 226 thereof. The deployment opening 232 is shaped and dimensioned to permit the deployment of the staples 212 from within the shaft 222, out of the deployment opening 232 and into adjacent tissue. The deployment opening 232 is located at the distal end 226 of the shaft 222 and extends through the side of the shaft 222 adjacent a closed, distal tip 234 thereof.

Referring to FIGS. 13-19, and as discussed above, a mechanism holding a staple 212 in position adjacent the deployment opening 232 is disclosed. Briefly, a locking bar 330 slides over the support post 304 and staple 212 to lock the staple in place prior to firing. The locking bar 330 holds the central portion along the body segment 278 of the staple 212 in place during firing. The locking bar 330 is pulled back just after firing prior to disengagement from tissue.

In the event a cartridge design is employed, a shuttle advancing mechanism design would be used to shuttle staples from within the proximal shaft to the firing position. At the firing position they would be shifted out of the delivery plane downward around and into the box 96.

In accordance with a preferred embodiment, the shaft 222 has a diameter that is less than approximately 5 mm to allow for insertion of the shaft 222 through a cannula or trocar (not shown) during an endoscopic or laparoscopic surgical procedure. As will be appreciated based upon the following disclosure, the trigger 220 facilitates both the advancement of a staple 212 through the shaft 222, as well as the deployment of the surgical staple 212 from the distal end 226 of the shaft 222. In accordance with an alternate embodiment, it is contemplated separate triggers or activating mechanisms may be incorporated into the surgical stapler for conveying a staple through the shaft and deploying the staple externally from the shaft and through the deployment opening into adjacent tissue.

In a surgical application, the surgical stapler 210 is manipulated through a trocar or endoscope to a desired location where the deployment opening 232 along the distal end 226 of the shaft 222 is pushed against the tissue area to be fastened. To facilitate placement of the deployment opening 232 against a selected tissue area, the shaft 222 is rotatably secured to the handle 216 and a rotating knob 236 is provided on the handle 216. The knob 236 includes a centralized bore 238 through which the shaft 222 extends. A boss (not shown) in the interior of the knob bore 238 engages a notch or slot (not shown) on the exterior surface (not shown) of the shaft 222. As the knob 336 is rotated, the shaft 222 is in turn rotated by the interaction of the knob boss with the shaft 222. As shaft 222 rotates, the location of the deployment opening 232 changes circumferentially relative to the surrounding tissue, thereby repositioning the deployment opening 232 against different areas of tissue. It will be appreciated that a connection also exists between the rotating knob 236 and the staple deploying assembly 228 inside of the shaft 222, so that rotation of the knob 236 also produces rotation of the staple deploying assembly 228 about the longitudinal axis of the shaft 222. Referring to FIGS. 5A, 5B, 6, 7A and 7B as described above with reference to the prior embodiment disclosed with reference to FIGS. 1 to 4, a mechanism is disclosed for utilizing the rotating knob 236 to turn the staple deploying assembly 228 without turning the handle 216 at the proximal end of the surgical stapler 210 and while allowing the trigger 220 to be used in the actuation of the staple deploying assembly 228. In accordance with a preferred embodiment of the present invention, the firing of the staple 212 is accomplished with either a push or pull motion down the axis of the shaft 222. This linear motion is connected to a trigger 220 to generate enough leverage to form the staple 212 as described below in greater detail. Between the trigger 220 and the rotating portion of the device, that is, the staple deploying assembly 228 this motion must be allowed to rotate so that the rotation does not require a user to turn his or her wrist to align the deployment opening 232 of the staple deploying assembly 228 to the tissue.

In accordance with a preferred embodiment, a snap ring is used to link the distal end of the shaft 222 to the staple deploying assembly 228, in particular, an attachment post extending from a proximal end of the staple deploying assembly. The snap ring includes recesses for engaging projection along the attachment post ensuring that rotation of the shaft will cause rotation of the attachment post in a manner desired by users of the present surgical stapler 10. In accordance with an alternate embodiment, a set screw is used to link the shaft 222 to the attachment post in a manner facilitating rotation in accordance with the present invention. Whether a snap ring or a setscrew is used, the shaft is secured to the trigger via a yoke that allows rotation of the attachment post relative to the trigger, while also permitting linear movement of the attachment post as the trigger is actuated to form a staple in accordance with the present invention. The staple deploying assembly 228 of this embodiment employs a staple 212 that is again aligned longitudinally within the shaft 222 opposite the lateral deployment opening 232. Aligning the staple 212 longitudinally allows a large staple 212 to be discharged through a small diameter shaft 222. A first staple driver 244 extends longitudinally through the shaft 222 beyond the distal prong 280 of the staple 212. The first staple driver 244 includes a proximal end 246 connected to a drive assembly and a distal end 248 with a proximally facing camming surface 250. A second staple driver 256 is located proximal of the staple 212, adjacent the proximal staple prong 282. The second staple driver 256 includes a proximal end 258 connected to a drive assembly and a distal end 260 with a distally facing camming surface 262. As shown with reference to FIGS. 13-19, the angled surfaces of the first staple driver 244 and the second staple driver 256 allow the camming surfaces 250, 262 to come together more fully and allow more angled formation of the staple 212. The staple still forms on the angle surface, the added notch feature simply helps to make the camming surfaces come together.

As with the prior embodiment, the staple 212 includes a long body segment 278 having a longitudinal axis. First and second prongs 280, 282 are found at opposite ends of the body segment 278 and extend in a direction that is substantially transverse to the longitudinal axis of the body segment 278. The first and second prongs 280, 282 extend in substantially the same direction. In accordance with a preferred embodiment, the first and second prongs 280, 282 are preferably bent at a 90° angle from the body segment 278 to facilitate entry of the staple 212 into tissue during firing. Each of the first and second prongs 280, 282 includes sharpened end points for piercing the tissue.

A series of four approximately 90° bends 288, 290, 292, 294 are formed in the midsection of the body segment 278. These bends 288, 290, 292, 294 within the body segment 278 form a "box" 296 area at the center of the staple 212. The bends 288, 290, 292, 294 are formed in the body segment 278 such that the plane of the box 296 is perpendicular to the plane in which the first and second prongs lie 280, 282. The box 296 divides the body segment 278 into a pair of legs 298, 300. The box 296 facilitates the advancement of a staple 212 through the shaft 222 into the deployment position opposite the deployment opening 232. Additionally, the box 296 provides control over a staple 212 as the staple 212 is shaped during deployment.

As with the prior embodiment a support post 304 is provided for supporting the staple 212 at the box 296 as the staple 212 is conveyed and bent during deployment. The support post 304 has a rectangular shape which mates with the similarly shaped box formation of the staple. In particular, the support post 304 includes four upwardly extending sidewalls 306, 308, 310, 312 and is shaped to sit within the spaced defined by the box 296 formed along the central portion of the body segment 278. The fit between the support post 304 and the box 296 is tight enough to maintain the staple 212 in a fixed position during conveying and bending, yet not so secure that the staple 212 cannot be released from the support post 304 after bending. In accordance with a preferred embodiment, the support post 304 is formed on the distal end 314 of a pushrod 316 (not shown) that is driven longitudinally through the shaft 222 between the staple cartridge and the deployment opening 232.

Referring to FIGS. 13-19 a mechanism for this process is disclosed. Briefly, a locking bar 330 slides over the support post 304 and staple 212 to lock the staple 212 in place prior to firing. The locking bar 330 holds the central portion along the body segment 278 of the staple 212 in place during firing. The locking bar 330 is pulled back just after firing prior to disengagement from tissue. In the event a cartridge design is employed, a shuttle advancing mechanism design would be used to shuttle staples from within the proximal shaft to the firing position. At the firing position they would be shifted out of the delivery plane downward around and into the box 96.

To fire a staple 212 in accordance with this staple deploying assembly 228, the trigger 220 is manually pivoted toward the pistol grip 218 to apply a firing force to the first and second staple drivers 244, 256. As this firing force is applied to the first and second staple drivers 244, 256, the first staple driver 244, is propelled proximally towards one side of the staple 212, while the second staple driver 256 is propelled distally towards the other side of the staple 212. As the respective first and second staple drivers 244, 256 converge against opposite sides of the staple 212, the respective camming surfaces 250, 262 of the first and second staple drivers 244, 256 engage the angled prongs 280, 282 of the staple 212. Because the midsection of the staple 212 is locked in position by the support post 304 within the box 296, the contact between camming surfaces 250, 262 of the first and second staple drivers 244, 256 and the angled prongs 280, 282 of the staple 212 produces a bending action in the sides or legs 298, 300 of the staple 212. The central portion of the staple 212 is constrained with the box 296 and the locking bar 330. As the staple drivers 244, 256 converge against opposite sides of the staple 212 the bending must take place in the unconstrained portion of the staple leg. As the first and second staple drivers 244, 256 continue converging on the sides of the staple 212, the sides of the staple 212 bend towards each other through the deployment opening 232, forcing the respective first and second prongs 280, 282 into the adjacent tissue. When the first and second staple drivers 244, 256 are driven into their proximal most and distal most positions, as shown in FIGS. 11 and 12, the staple 212 is fully bent so that the sides of the body segment 278 extend perpendicular to box 296 through the deployment opening 232. In this position, the first and second prongs 280, 282 are bent fully within the tissue layers to form a closed link, locking the layers of tissue together. Like the first embodiment disclosed above with reference to FIG. 1 to 4, this second staple deploying assembly 228 enables large staples 212 to be discharged through a side deployment opening 232 of a slender shaft 222. However, in this assembly, the first and second staple drivers 244, 256 act directly upon the sides of the staple 212, eliminating the need for bending arms.

FIGS. 20-35 depict a third embodiment of a staple deploying assembly 428 in accordance with the present invention. As with prior embodiment as shown with reference to FIGS. 1 to 4, the surgical stapler 410 includes a handle 416 having a pistol grip 418 shaped for gripping by a surgeon. A trigger 420 is movably coupled to the handle 416 to be drawn toward the pistol grip 418 during staple deployment. As will be appreciated based upon the following disclosure, first and second slide-able rotation knobs 526, 528 are included on the handle 416. The most distal rotation knob, that is, the first rotation knob 526, controls either a rod or a cable attached to the staple rotation knob. The second proximal mounted rotation knob 528 controls the staple former 462 rotation; either a rod or a cable will be attached to the anvil rotation knob 528 to actuate the rotating anvil at the distal end of the surgical stapler 410. Once both knobs 526, 528 have been rotated 90 degrees the distal staple rotation block and the rotating anvil are locked into a position perpendicular to the axis of the surgical stapler 410. In this position the trigger 420 is engaged with the firing assembly to bring the anvil in contact with the staple and form the legs of the staple into an axis parallel with the axis of the surgical stapler 410.

An elongated, tubular shaft 422 extends distally from the handle 416. The tubular shaft 422 includes a proximal end 424 secured to the handle 416 and an open distal end 426 from which staples 412 are deployed in accordance with the present invention and as discussed below in greater detail.

A staple deploying assembly 428 is disposed within the interior 430 of the shaft 422 for discharging staples 412 from the distal end 414 of the surgical stapler 410. In accordance with a preferred embodiment, the shaft 422 has a diameter that is less than approximately 5 mm to allow for insertion of the shaft 422 through a cannula or trocar (not shown) during an endoscopic (that is, procedures performed through a natural orifice, for example, transorally) or laparoscopic (that is, procedures performed through a surgically created opening, for example, via a trocar) surgical procedure. As will be appreciated based upon the following disclosure, the trigger 420 (or other activating mechanisms, such as sliding rotational knobs, levers or other control mechanisms as commonly used in surgical tools) facilitates both the advancement of a staple 412 through the shaft 422, as well as the deployment of the surgical stapler 410 from the open distal end 426 of the shaft 422. In accordance with an alternate embodiment, it is contemplated separate triggers or activating mechanisms may be incorporated into the surgical stapler for conveying a staple through the shaft and deploying the staple externally from the shaft and through the deployment opening into adjacent tissue.

In accordance with this embodiment, the shaft 422 includes an open distal tip 434 at the open distal end 426 thereof for discharging staples 412, rather than a side deployment opening as in the previous embodiments. A staple 412 is advanced longitudinally completely through the shaft 422 for deployment through the open distal tip 434 of the shaft 422. In a surgical application, the surgical stapler 410 is manipulated through a trocar or endoscope to a desired location where the open distal tip 434 of the shaft 422 is pushed against the tissue area to be fastened. More particularly, the staple 412 is rotated into firing position prior to advancing the staple 412 into tissue for firing. In practice, it is contemplated a set of graspers would be used to bring a tissue fold or plication together, then the staple is applied across the fold of tissue and staple is then formed to secure the tissue fold together.

As shown in FIGS. 20-35 the staple deploying assembly 428 includes an staple rotation block 444 for conveying a staple 412 through the shaft 422. The staple 412 is substantially the same as described above with regard to the embodiment shown with reference to FIGS. 1 to 4. The staple rotation block 444 includes a center support post 446 that engages the box 496 of the staple 412 to hold the staple 412 during transport through the shaft 422. The staple rotation block 444 is conveyed through the shaft 422 by a lower push rod 448. The lower push rod 448 extends axially through the length of the shaft 422. The lower push rod 448 includes a proximal end 450 and a distal end 452 to which the staple rotation block 444 is secured. The proximal end 450 of the lower push rod 448 is attached to a driving assembly in the handle 416. The drive assembly functions in a manner similar to that described above with regard to the previously disclosed embodiments. A support 454 pivotally connects the staple rotation block 444 to the lower push rod 448, and allows the staple rotation block 444 to rotate relative to the push rod 448 under the control of the first rotation knob.

The staple rotation block 444 has a rectangular shape and includes first and second bending guides 456, 458 on the longer ends of the staple rotation block 444. The first and second bending guides 456, 458 provide a structure around which the staple 412 is formed during deployment.

The staple rotation block 444 has a rectangular shape and includes first and second bending guides 456, 458 on the longer ends of the staple rotation block 444. The first and second bending guides 456, 458 provide a structure around which the staple 412 is formed during deployment. When held by a center support, the box 496 of the staple 412 passes between the first and second bending guides 456, 458. The legs 498, 500 of the staple 412 are longer than the first and second bending guides 456, 458, so that the prongs 480, 482 of the staple 412 can be wrapped around the first and second bending guides 456, 458 during deployment.

An staple former 462 is driven along the longitudinal axis of the shaft 422 to facilitate the staple 412 bending around the first and second bending guides 456, 458 during deployment. The staple former 462 includes first and second forming blocks 464, 466 attached on opposite sides of a connecting member 468. Each of the first and second forming blocks 464, 466 include a facing surface 470, 472 shaped and dimensioned to engage the staple 412 during the bending procedure as discussed below in greater detail. The distance between the first and second forming blocks 464, 466 is greater than the longer length of the staple rotation block 444, so that the first and second forming blocks 464, 466 can move past the respective first and second bending guides 456, 458 on the staple rotation block 444. The staple former 462 is driven axially within the shaft 422 by a longitudinally extending, upper push rod 474. The upper push rod 474 extends substantially through the length of the shaft 422 and is connected at a proximal end 476 to a driving assembly. The staple former 462 causes the legs 498, 500 of the staple 412 to be wrapped around the first and second bending guides 456, 458 during deployment.

The staple former 462 is driven along the longitudinal axis of the shaft 422 to facilitate the staple 412 bending around the first and second bending guides 456, 458 during deployment. The staple former 462 includes first and second forming blocks 464, 466 attached on opposite sides of a connecting member 468. Each of the first and second forming blocks 464, 466 include a facing surface 470, 472 shaped and dimensioned to engage the staple 412 during the bending procedure as discussed below in greater detail. The distance between the first and second forming blocks 464, 466 is greater than the longer length of the staple rotation block 444, so that the first and second forming blocks 464, 466 can move past the respective first and second bending guides 456, 458 on the staple rotation block 444. The staple former 462 is driven axially within the shaft 422 by a longitudinally extending, upper push rod 474. The upper push rod 474 extends substantially through the length of the shaft 422 and is connected at a proximal end 476 to a driving assembly, as indicated by arrow. The staple former 462 is secured at the distal end 520 of the upper push rod 474. The upper push rod 474 includes an opening extending perpendicular to the length of the upper push rod 474. An attachment member 524 extends from the staple former 462 through the opening 522 to connect the staple former 462 to the upper push rod 474, and provide a vehicle for rotating the staple former 462 relative to the upper push rod 474. The upper push rod 474 extends parallel to the lower push rod 448 along the longitudinal axis of the shaft 422. The upper push rod 474 is spaced from the lower push rod 448 by the staple former 462. The staple former 462 slides along the surface of the lower push rod 448 as the staple former 462 is propelled distally through the shaft 422. It is contemplated a rotation lock may be used to prevent any rotational movement of the staple former and/or staple rotation block during the firing and bending of the staple. It is contemplated this may be accomplished with a frictional locking mechanism, or a notch, wherein the parts lock together like a gear tooth when enough force is exerted on the assembly. A locking bar could slide forward to lock both features prior to staple deployment.

Prior to insertion of the surgical stapler 410 into the body, a staple 412 is loaded onto the staple rotation block 444 by advancing the lower push rod 448 to a fully distal position beyond the open distal end 426 of the shaft 422. With the staple rotation block 444 outside of the shaft 422, a staple 412 is loaded into the surgical stapler 410 by pressing the box 496 of the staple 412 against the center support 460 until the sides of the box 496 are in contact with the support. After a staple 412 is loaded, the lower push rod 448 is retracted back inside of the shaft 412 to draw the staple rotation block 444 and the attached staple 412 into the interior of the stapler shaft 422. The staple rotation block 444 and staple 412 are retracted into the shaft 422 with the longitudinal length of each extending along the axis of the shaft 422. Loading the staple 412 in this fashion enables a much longer staple 412 to be loaded into the small diameter stapler shaft 422. When retracted, the distal prong 480 of the staple 412 is located just inside of the open distal end 426 of the shaft 422.

With the staple rotation block 444 and the attached staple 412 inside the shaft 422, the surgical stapler 410 is inserted through a small diameter trocar port or endoscope to reach tissue inside a body cavity. At the appropriate tissue location, the trigger 420 is manually actuated to drive the lower push rod 448 distally and expose the full length of the staple 412 outside the open distal end 426 of the shaft 422. Outside of the shaft 422, the staple rotation block 444 is rotated 90° under the control of the first rotation knob to orient the staple 412 perpendicular to the axis of the shaft 422 and position the staple prongs 480, 482 against the adjacent tissue, as shown in FIGS. 20 to 35. With the staple 412 aligned against the tissue, the staple former 462 is driven distally by the upper push rod 474 through the open distal end 426 of the shaft 422. Outside of the shaft 422, the staple former 462 is also rotated 90° under the control of the second rotation knob to align the length of the staple former 462 in parallel with the length of the exposed the staple 412. The staple former 462 is driven proximally by the upper push rod 474 along the sides of the staple rotation block 444, as shown in FIG. 23.

As the staple former 462 passes along the sides of the staple rotation block 444, the facing surfaces 470, 472 along the first and second forming blocks 464, 466 on the sides of the staple former 462 push against and bend the legs 498, 500 of the staple 412 inwardly, driving the staple prongs 480, 482 and legs 498, 500 into the tissue layers or folds of tissue securing a plication. The staple former connecting member 468 has a thin height relative to the first and second forming blocks 464, 466, which enables the connecting member 468 to pass over the staple 412 and staple rotation block 444 as the first and second forming blocks 464, 466 push against and bend the sides of the staple 412. After the staple 421 has been pushed fully into the tissue layers, the center support post 446 is retracted away from box 496 to release the staple 412 from the surgical stapler 410. After the staple 412 is released, the staple former 462 is rotated back into longitudinal alignment with the shaft axis, and drawn proximally back into the interior 430 of the shaft 422 by upper push rod 474. The staple rotation block 444 is also rotated back into longitudinal alignment with the shaft axis and retracted proximally into the shaft 422. After both the staple former 462 and the staple rotation block 444 are stowed inside of the shaft 422, the surgical stapler 410 can be removed from the body to complete the procedure, or reloaded with another staple 412 to further secure the tissue layers. A staple feeding means can also be used to continuously feed staples into the distal end of the device.

Figure 36A:
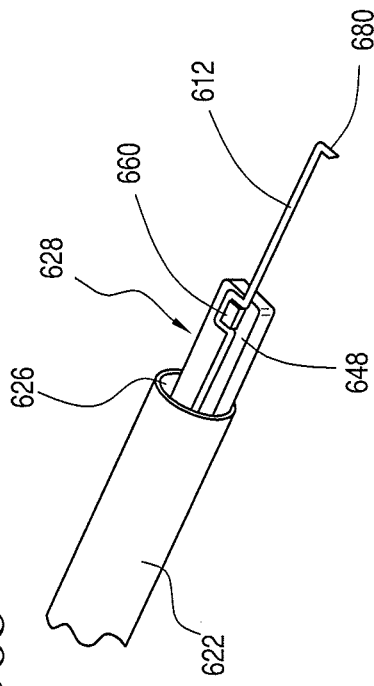
Figure 36B:
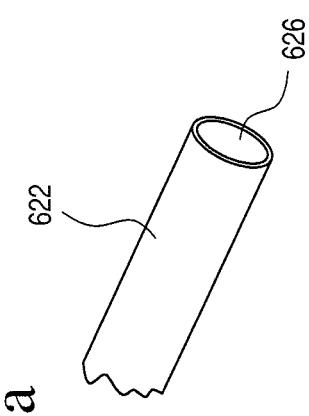
Figure 36C:
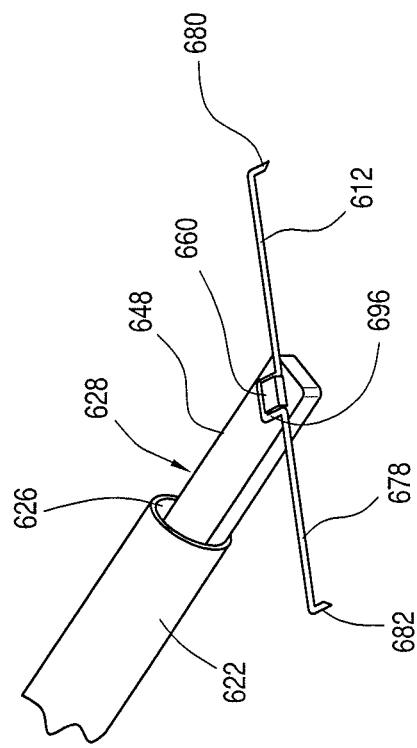
Figure 36D:
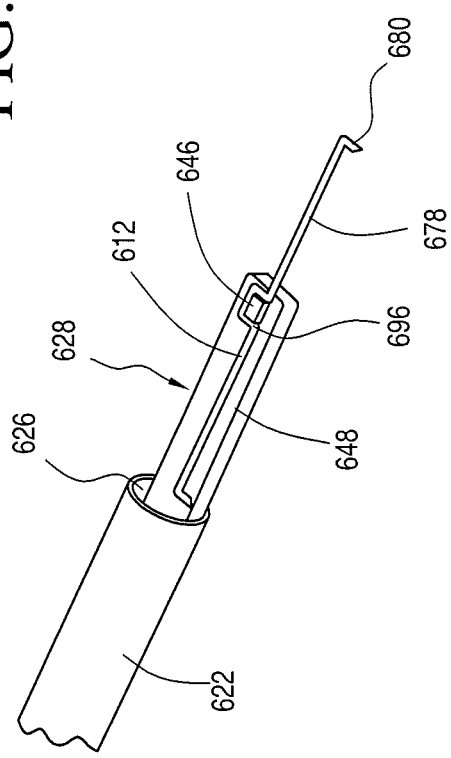

FIG. 36A-36H illustrate another embodiment of a staple deploying assembly 628 in accordance with the present invention and which is similar to the staple deploying assembly disclosed above with reference to FIGS. 20-35. The staple deploying assembly 628 advances the staple 612 longitudinally out an open distal end 626 of the stapler shaft 622. In accordance with this embodiment, the staple 612 is attached to a lower push rod 648 by a center support post 646. The lower push rod 648 conveys the staple 612 longitudinally along the shaft axis and out the open distal end 626 of the shaft 622, as shown in FIGS. 36B to 36H. With the full length of the staple 612 extended outside of the shaft 622, as shown in FIG. 36C, the staple 612 is rotated 90° by the center support post 646, as shown in FIGS. 36D and 36E. When the staple 612 is fully rotated, the body segment 678 of the staple 612 is transverse to the axis of the surgical stapler shaft 622, as shown in FIG. 36E. With the surgical stapler 610 rotated, the prongs 680, 682 of the staple 612 face the adjacent targeted tissue (not shown). To drive the prongs 680, 682 into the tissue, a staple former 662 is advanced distally through the shaft 622 and outside the open distal end 626. The staple former 662 has first and second vertical members 664, 666 separated by a thin connecting member 668. Each of the first and second vertical members 664, 666 include a facing surface 670, 672 shaped and dimensioned to engage the staple 612 during the bending procedure as discussed below in greater detail. As the staple former 662 is advanced distally, the facing surfaces 670, 672 of the first and second vertical members 664, 666 push against the staple 612 on the sides of the box 696 to bend the staple legs 698, 700 in a forward direction, as shown in FIG. 36G. When the staple former 662 is fully extended, the staple 612 is bent so that the prongs 680, 682 are drawn through the tissue and into an overlocking engagement, as shown in FIGS. 36G and 36H. Following formation of the staple 612, the staple former 662 is retracted proximally back inside of the shaft 622, as shown in FIG. 36H. The staple 612 is then released from the center support post 646 by twisting the stapler shaft 622 so that the surgical stapler 610 is pulled away from the support. Alternatively, to release the staple, a mechanism (not shown) may be provided to draw the support downwardly into the push rod to disengage the support from the box. After the staple is released, the lower push rod is pulled proximally back inside of the stapler shaft.

Figure 37:
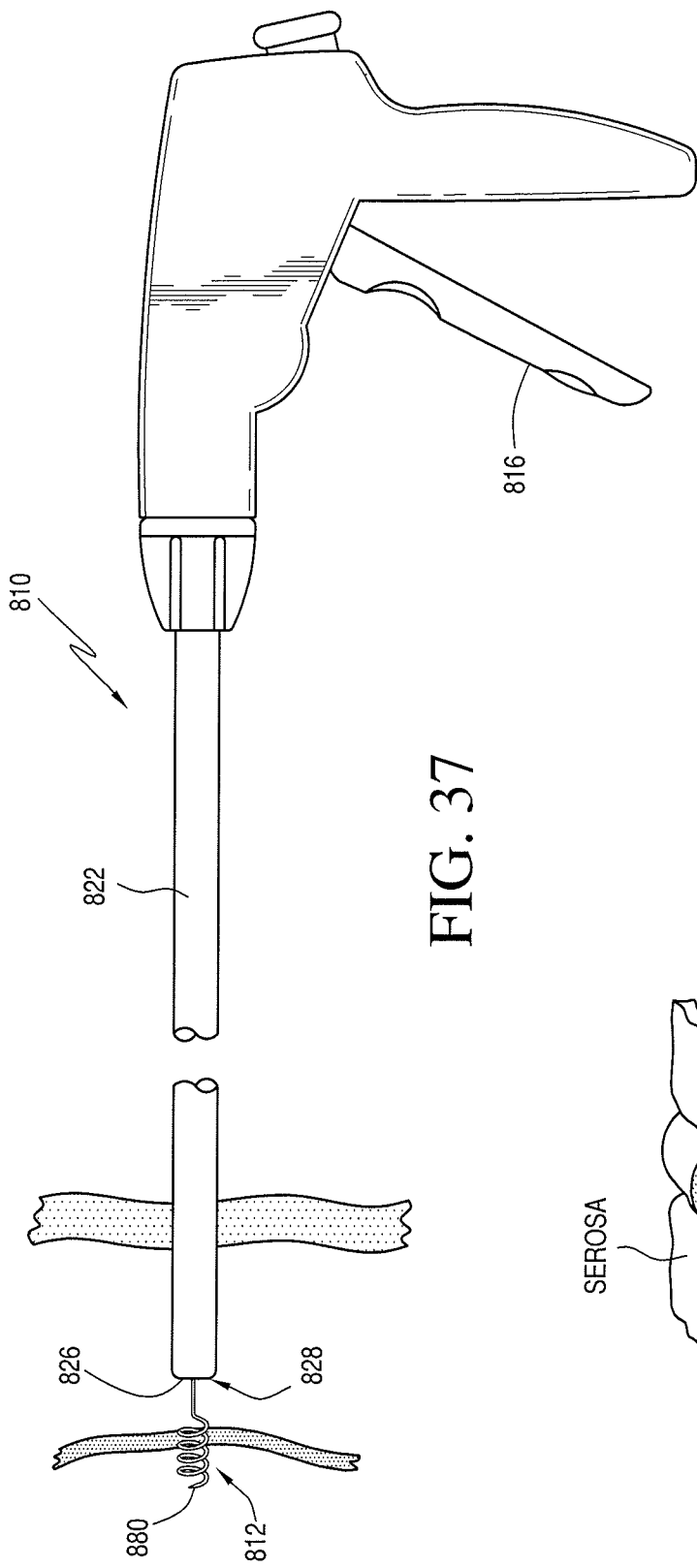
FIG. 37 is a side view of a low-profile surgical stapler showing a fifth staple deploying assembly embodiment.
Figure 38:
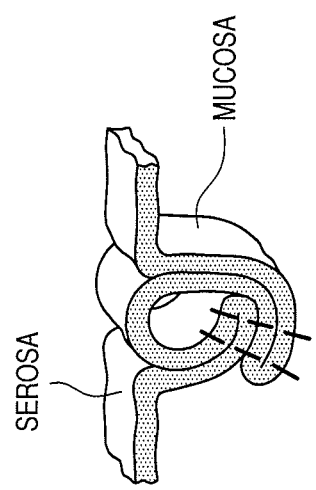
FIG. 38 is a schematic diagram of a double tissue fold formed from the walls of the stomach cavity.
Figure 40:
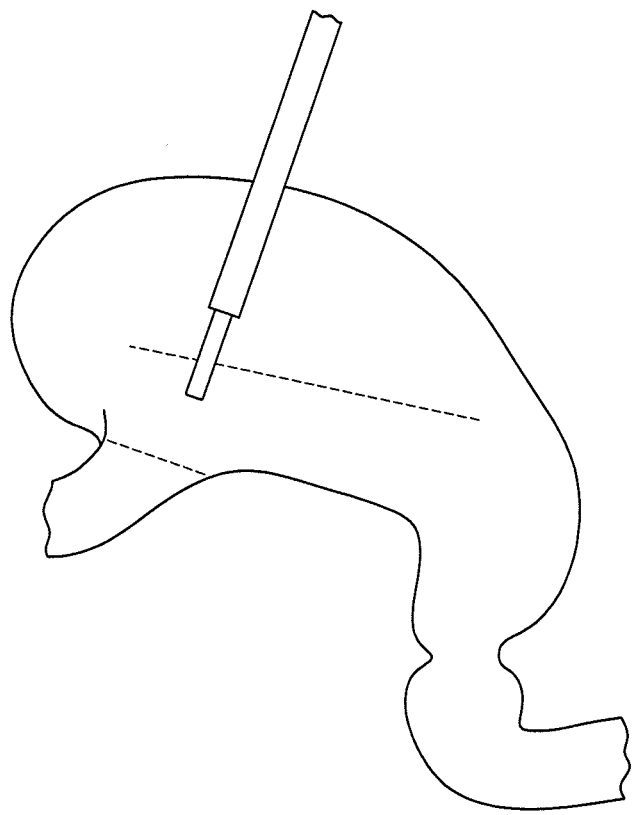
FIG. 40 is a schematic diagram showing the fourth staple deploying assembly embodiment during a gastric volume reduction procedure.

FIG. 37 depicts yet another embodiment of a staple deploying assembly 828 in accordance with the present invention. In accordance with this embodiment a helical staple 812 is deployed to fasten multiple tissue layers together. The staple 812 is deployed axially out an open distal end 826 of a shaft 822. The staple 812 is preferably a 3/16" diameter coil comprised of Nitinol, or other shape memory material, that is drawn out into a helical shape. The surgical stapler 810 includes a sharpened tip 880 on the end of the coil 812 facing the discharge opening, that is, the open distal end 826, of the stapler shaft 822. To fasten tissue layers together, the slender, tubular shaft 822 is passed through a small (5 mm) trocar and into the abdominal cavity. Within the cavity, the surgical stapler 810 is manipulated so that the open shaft end 826 is against the tissue layers to be fastened. The trigger 816 is then actuated to eject the sharpened tip 880 of the staple 812 through the shaft opening 826 and pierce the tissue. With the tip 880 lodged in the tissue, the driving mechanism of the surgical stapler 810 is rotated to turn the helical curves of the staple 812 and drive the staple tip 880 further into the tissue. Once the staple 812 has been driven fully into the tissue layers, the staple 812 is released from the surgical stapler 810.

Turning attention now to an exemplary application of the low profile surgical stapler in a gastric volume reduction (GVR) procedure for the treatment of morbid obesity. This gastric volume reduction procedure involves the creation of a fold on the anterior of the stomach where the fold is inverted inside the stomach. The effect is that the space inside the stomach is taken up with this fold. A small sleeve like area is left where the food can pass distally through the volume reduced stomach. In this example, the sleeve is created by a double tissue fold. In a double tissue fold, tissue along the two sides of the lesser curve of the stomach is drawn into the stomach cavity. In the cavity, one side of the tissue is folded and wrapped around an endoscope tube, or other tubular structure, that has previously been introduced into the stomach cavity. A second portion of the stomach wall from the opposite side of the tube is then drawn into the stomach cavity, folded, and pulled back across the endoscope tube, overlaying the first fold of tissue. The first and second folds of tissue are secured together to form a double fold sleeve, such as shown in Figure -. In a double tissue folding procedure such as this, the two individual folds need to be fastened extremely well to allow the contacting mucosa layers to heal together. Since the double fold involves essentially four layers of tissue drawn together, a large fastener is required in order to securely fasten all four layers. In the past, delivering a fastener of sufficient size to secure all the tissue layers required a large trocar or open incision in order to pass a large enough surgical stapler into the cavity. Using a low profile surgical stapler, the multiple tissue layers can be secured together, as indicated at, with a large staple advanced through a much smaller trocar port.

To secure the multiple layers of gastric tissue together, the shaft of the surgical stapler is inserted through a 5 mm trocar which has been placed through the abdominal and gastric walls. The distal tip of the surgical stapler is inserted into the stomach cavity and manipulated into position near the lesser curve. During this procedure, a flexible gastroscope is passed transesophageally into the stomach cavity to provide insufflation, illumination and visualization within the cavity. Figure - illustrates a low profile surgical stapler employing either of the first or second staple deploying assembly embodiments to eject a staple from the side of the staple shaft inside a stomach cavity. As shown in this Figure, the surgical stapler is manipulated so that the deployment opening is adjacent to the double tissue fold, indicated symbolically by the line. In this position, one or more staples are fired through the opening to securely fasten the fold. The shaft can be moved or rotated after each deployment to secure the fold at multiple locations. After the fold is secure, the shaft can be removed through the trocar port.

Figure 39:
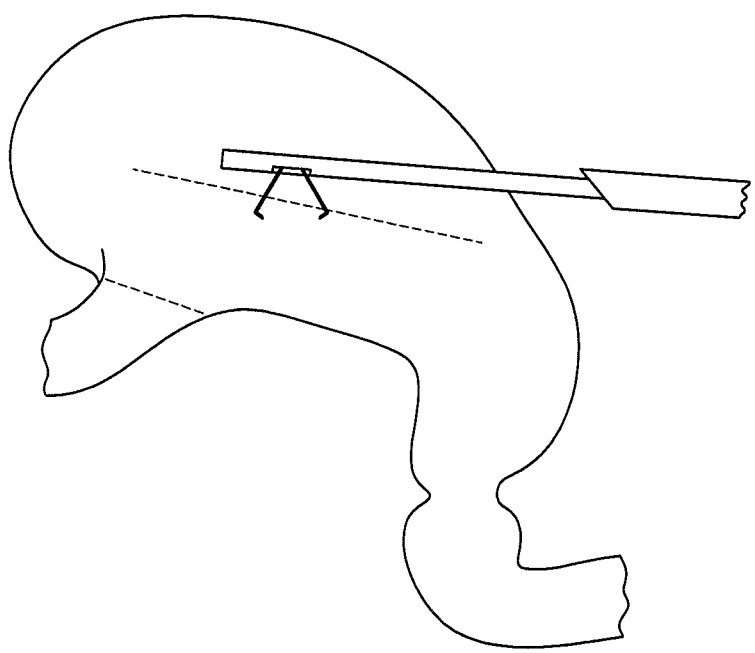
FIG. 39 is a schematic diagram showing the first or second staple deploying assembly embodiments during a gastric volume reduction procedure.

FIG. 39 shows a low profile surgical stapler employing the staple deploying assembly of the embodiment shown with reference to FIGS. 1 to 19, to discharge a staple into a tissue fold. In this embodiment, the stapler shaft is inserted through a 5 mm trocar placed in the abdominal wall. The distal tip of the surgical stapler is inserted into the stomach cavity and manipulated into position near the lesser curve. The surgical stapler is positioned so that the open distal tip of the shaft is adjacent to the targeted fastening location in the tissue fold. Once positioned adjacent the fold, a staple is fired through distal open shaft tip, in the manner described above, to fasten the fold. The shaft can be repositioned through the trocar after each deployment to secure the fold at multiple locations.

In the present invention, a large staple is conveyed longitudinally through a small diameter discharge shaft. The staple is discharged either through the side of the shaft, or rotated and fired out the distal tip of the shaft. By transferring the body of the staple longitudinally, rather than transversely, through the stapler shaft, a larger size staple can be discharged through a smaller size opening than previously possible. Being able to apply large staples through small, minimally invasive surgical openings enables larger areas of tissue to be joined together while reducing the trauma and recovering time of the patient.

A hybrid endoscopic/laparoscopic surgical procedure has been developed for involuting the gastric cavity wall to reduced stomach volume. In the hybrid gastric volume reduction (GVR) procedure, pairs of suture anchoring devices are deployed through the gastric cavity wall. Following deployment of the anchors, suture attached to each pair of anchors is cinched and secured to involute the cavity wall. This procedure is described in greater detail in commonly owned and co-pending U.S. patent application Ser. No. 11/779,314, filed Jul. 18, 2007, entitled "HYBRID ENDOSCOPIC/LAPAROSCOPIC DEVICE FOR FORMING SEROSA TO SEROSA PLICATIONS IN A GASTRIC CAVITY", and Ser. No. 11/779,322, FILED Jul. 18, 2007, entitled "HYBRID ENDOSCOPIC/LAPAROSCOPIC METHOD FOR FORMING SEROSA TO SEROSA PLICATIONS IN A GASTRIC CAVITY", which are hereby incorporated herein by reference. One skilled in the art will recognize that the novel inventions described herein are well suited for fastening apposed tissue surfaces together. In particular it is envisioned that the devices described herein are well suited to perform this gastric reduction procedure.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A low-profile surgical stapler that enables a large-sized staple to be delivered into a body cavity through a small opening or port, comprising:
   a handle having a trigger movably coupled to the handle;
   an elongated, tubular shaft having a longitudinal axis and extending distally from the handle, the tubular shaft includes a proximal end secured to the handle and a distal end in which a deployment opening is formed;
   a staple deploying assembly is disposed within an interior of the shaft for discharging staples from the deployment opening at the distal end of the shaft, the staple deploying assembly supporting a staple such that a longitudinal axis of the staple is aligned with a longitudinal axis of the shaft, the staple having a length dimension bigger than a diameter of the shaft, the staple, prior to deployment, includes a long body segment having a longitudinal axis and first and second prongs, with sharpened end tips, extending transversely from opposite ends of the body segment;
   the body segment of the staple includes a first leg and a second leg, and the staple deploying assembly includes a first staple driver and a second staple driver extending longitudinally through the shaft, the first staple driver acting upon the first leg of the staple to bend the first leg relative to the second leg and the second staple driver acting upon the second leg of the staple to bend the second leg relative to the first leg;
   wherein the deployment opening is shaped and dimensioned to permit deployment of the staples from within the shaft, out of the deployment opening and into adjacent tissue.

2. The surgical stapler according to claim 1, wherein the shaft has a diameter that is less than approximately 5 mm.

3. The surgical stapler according to claim 1, wherein the shaft is rotatably secured to the handle.

4. The surgical stapler according to claim 3, wherein rotation of the shaft is coordinated with rotation of the staple deploying assembly.

5. The surgical stapler according to claim 1, wherein the first staple driver includes a camming surface that is shaped to act upon the first leg of the staple and the second staple driver includes a camming surface shaped to act upon the second leg of the staple.

6. The surgical stapler according to claim 1, wherein first and second bending arms are longitudinally disposed in the shaft and oriented in a manner facing the deployment opening such that a staple may be supported thereon during folding and subsequent ejection from the deployment opening.

7. The surgical stapler according to claim 6, wherein the first staple driver includes a camming surface that is shaped to act upon the first bending arm for bending of the first leg and the second staple driver includes a camming surface shaped to act upon the second bending arm for bending the second leg.

8. A low-profile surgical stapler that enables a large-sized staple to be delivered into a body cavity through a small opening or port, comprising:
- a handle having a trigger movably coupled to the handle;
- an elongated, tubular shaft having a longitudinal axis and extending distally from the handle, the tubular shaft includes a proximal end secured to the handle and a distal end in which a deployment opening is formed;
- a staple having a longitudinal axis aligned with the longitudinal axis of the shaft, the staple also having a length dimension bigger than a diameter of the shaft, the staple, prior to deployment, includes a long body segment having a longitudinal axis and first and second prongs, with sharpened end tips, extending transversely from opposite ends of the body segment, wherein the body segment includes a box at a center of the staple;
- a staple deploying assembly is disposed within an interior of the shaft for discharging the staple from the deployment opening at the distal end of the shaft, the staple deploying assembly supporting the staple such that the longitudinal axis of the staple is aligned with the longitudinal axis of the shaft;
- wherein the deployment opening is shaped and dimensioned to permit deployment of the staples from within the shaft, out of the deployment opening and into adjacent tissue.

9. The surgical stapler according to claim 8, wherein the staple deploying assembly includes a support post shaped and dimensioned to support the staple at the box.

10. A low-profile surgical stapler that enables a large-sized staple to be delivered into a body cavity through a small opening or port, comprising:
- a handle having a trigger movably coupled to the handle;
- an elongated, tubular shaft having a longitudinal axis and extending distally from the handle, the tubular shaft includes a proximal end secured to the handle and a distal end in which a deployment opening is formed;
- a staple deploying assembly is disposed within an interior of the shaft for discharging staples from the deployment opening at the distal end of the shaft, the staple deploying assembly supporting a staple such that a longitudinal axis of the staple is aligned with a longitudinal axis of the shaft, the staple, prior to deployment, includes a long body segment having a longitudinal axis and first and second prongs, with sharpened end tips, extending transversely from opposite ends of the body segment;
- wherein the deployment opening is shaped and dimensioned to permit deployment of the staples from within the shaft, out of the deployment opening and into adjacent tissue;
- wherein the body segment includes a box at a center of the staple and the staple deploying assembly includes a support post shaped and dimensioned to support the staple at the box; and
- further including a locking bar which selectively slides over the support post and staple to lock the staple in place prior to firing.

11. A low-profile surgical stapler that enables a large-sized staple to be delivered into a body cavity through a small opening or port, comprising:
- a handle having a trigger movably coupled to the handle;
- an elongated, tubular shaft having a longitudinal axis and extending distally from the handle, the tubular shaft includes a proximal end secured to the handle and a distal end in which a deployment opening is formed;
- a staple deploying assembly is disposed within an interior of the shaft for discharging staples from the deployment opening at the distal end of the shaft, the staple deploying assembly supporting a staple such that a longitudinal axis of the staple is aligned with a longitudinal axis of the shaft, the staple, prior to deployment, includes a long body segment having a longitudinal axis and first and second prongs, with sharpened end tips, extending transversely from opposite ends of the body segment;
- wherein the deployment opening is shaped and dimensioned to permit deployment of the staples from within the shaft, out of the deployment opening and into adjacent tissue and the deployment opening is at a distal tip of the shaft; and
- assembly includes an anvil including a center support that engages the staple to hold the staple during transport through the shaft.

12. The surgical stapler according to claim 11, wherein the anvil includes first and second bending guides providing a structure around which the staple is formed during deployment.

13. The surgical stapler according to claim 12, wherein the staple deploying assembly includes a staple former includes first and second forming blocks attached on opposite sides of a connecting member.

14. The surgical stapler according to claim 13, wherein each of the first and second forming blocks includes a facing surface shaped and dimensioned to engage the staple during a bending procedure.

* * * * *